(12) United States Patent
DePinho

(10) Patent No.: US 6,613,750 B2
(45) Date of Patent: Sep. 2, 2003

(54) METHOD OF INHIBITING CELL PROLIFERATION USING AN ANTI-ONCOGENE PROTEIN

(75) Inventor: Ronald A. DePinho, Pelham Manor, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/044,602

(22) Filed: Mar. 19, 1998

(65) Prior Publication Data

US 2002/0193325 A1 Dec. 19, 2002

(51) Int. Cl.$^7$ .................. A01N 43/04; A01N 63/00; C12N 15/63
(52) U.S. Cl. .................. 514/44; 435/455; 424/93.21
(58) Field of Search .................. 514/44, 1; 435/455; 424/93.21

(56) References Cited

U.S. PATENT DOCUMENTS

| | | | |
|---|---|---|---|
| 5,411,860 A | 5/1995 | Vogelstein et al. | 435/6 |
| 5,672,508 A | 9/1997 | Gyuris et al. | 435/320.1 |
| 5,702,908 A | 12/1997 | Picksley et al. | 435/7.8 |

OTHER PUBLICATIONS

Kaya et.al.; A single amino acid substitution results in a retinoblastoma protein defective in phosphorylation and oncoprotein binding, 1990, Proc. Natl. Acad. Sci., vol. 87: 6922–6926.*

Verma et.al.; Gene therapy– promises, problems and prospects, 1997, Nature, vol. 389: 239–242.*
Crystal; Transfer of Genes to Humans: Early Lessons and Obstacles to Success, 1995, Science, vol. 270: 404–410.*
Deonarain; Ligand–targeted receptor–mediated vectors for gene delivery, 1998, Exp. Opin. Ther. Patents 8(1): 53–69.*
J. Rudinger, Peptide Hormones, Edited by Oarsons, University Park Press, Baltimore, p. 1–7, 1976.*
Eck et al., Goodman & Gilman's The Pharmacological Basis of Therapeutics, Ninth Edition, McGraw–Hill, New York, p. 77–101, 1996.*
Kamijo et al., 1997, Cell, vol. 91, p. 649–659, Nov. 1997.*
Quelle et al., Oncogene, 11(4):635–645, Aug. 1995.
Quelle et al., Cell, 83:993–1000, Dec. 1995.
Scherr, C.J., Science, 274:1672–1677, 1996.
Serrano et al., Cell, 85(1):27–37, 1996.
Quelle et al., Proc. Natl. Acad. Sci. U.S.A., 94(2):669–673, 1997.

* cited by examiner

Primary Examiner—Shin-Lin Chen
(74) Attorney, Agent, or Firm—Amster, Rothstein & Ebenstein

(57) ABSTRACT

The present invention provides a novel method of inhibiting the growth of tumor cells based upon the discovery that $p19^{ARF}$ acts as a suppressor of oncogenic transformation by binding to the MDM2 oncoprotein and blocking MDM2's ability to target associated proteins, such as p53 and Rb, for proteosomal degradation. The method provided by the present invention inhibits the growth of a tumor cell by administering to the cell an effective amount of $p19^{ARF}$ or a mimetic thereof, and p53 to inhibit the growth of the tumor cell. Also provided by the present invention are pharmaceutical composition comprising $p19^{ARF}$ or a mimetic thereof, and/or p53.

2 Claims, 12 Drawing Sheets

Figure 5A
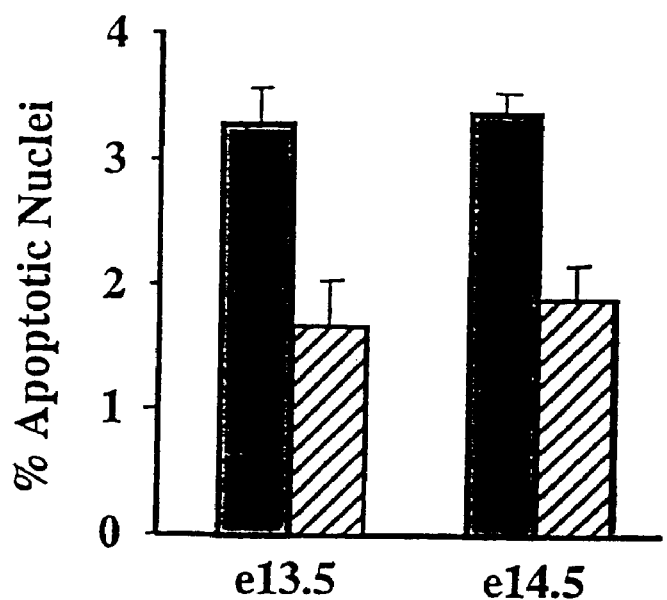
Figure 5B
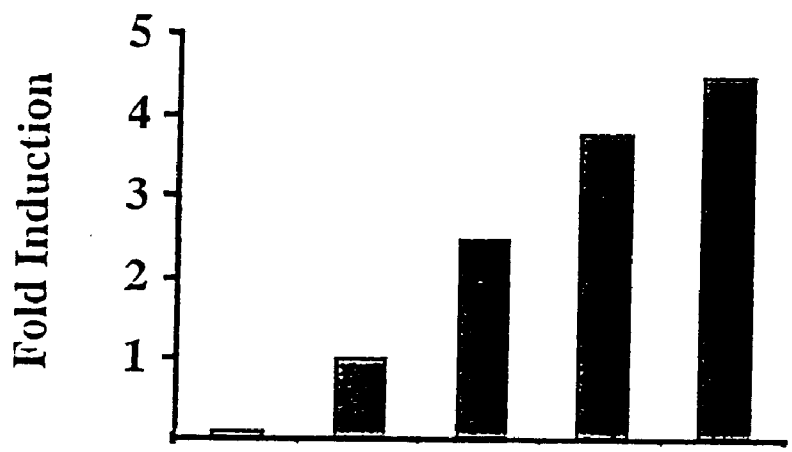
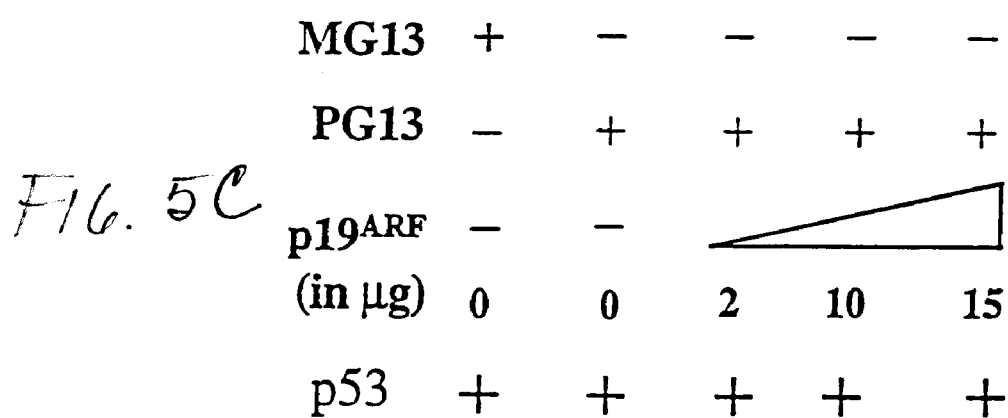
FIG. 5C

— REF assay —

— MEF assay —

METHOD OF INHIBITING CELL PROLIFERATION USING AN ANTI-ONCOGENE PROTEIN

STATEMENT OF GOVERNMENT INTEREST

This invention was made with government support under NIH Grant No. RO1EY09300. As such, the government has certain rights in this invention

BACKGROUND OF THE INVENTION

Growth control in mammalian cells is accomplished largely by the Rb protein regulating exit from the G1 phase (Weinberg, 1995, Cell 81, 323–330) and the p53 protein triggering growth arrest/apoptotic processes in response to cellular stress (Levine, 1997, Cell 88, 323–331). Cross-talk between these two regulatory pathways may be mediated through the p21 cdk inhibitor, which is a target of p53 transactivation as well as a factor that influences the functional status of Rb (Weinberg, 1995, Cell 81, 323–330.). An additional level of overlap between p53 and Rb is provided by the MDM2 protein that can physically associate with both proteins and prevent their growth suppression (Momand et al., 1992, Cell 69, 1237–1245; Xiao et al., 1995, Nature 375, 694–698). In tumorigenesis RB and p53 appear to serve collaborative roles as evidenced by the observations that many tumor types exhibit mutations in both RB and p53 (Williams et al., 1994, Nature Genet. 7, 480–484) and mice that are RB+/− and p53−/− develop a wider range of tumors at earlier ages than mice that are either Rb+/− or p53−/− (Williams et al., 1994, Nature Genet. 7, 480–484). Moreover, the ability of several viruses to transform cells in culture and cause tumors in mice is due to viral oncoproteins that bind to and inactivate both RB and p53 (Hawley-Nelson et al., 1989, EMBO 8, 3905–3910; Munger et al., 1989, Journal of Virology 63, 4417–4421; Mahon et al., 1987, Science 235, 1622–1628; Symonds et al., 1994, Cell 78, 703–711). The mechanistic basis for this dual requirement stems in part from the deactivation of a p53-dependent cell suicide program that would normally be brought about as a response to unchecked cellular proliferation resulting from Rb-deficiency (Ko and Prives, 1996, Genes Devel. 10, 1054–1072; Gottlieb and Oren, 1996, Biophysica Acta. 1287, 77–102; Levine, 1997, Cell 88, 323–331).

p53 mutation is thought to be the most frequent genetic alteration in human cancers (Hollstein et al., 1991, Science 253, 49–53; Levine et al., 1991, Nature 351, 453–456). In proliferating normal and neoplastic cells, the consequences of p53 overexpression are context-dependent, resulting in either cell cycle arrest or induction of apoptosis (Ko and Prives, 1996, Genes Devel. 10, 1054–1072). These biological endpoints provide a basis for p53's anti-oncogenic actions (Eliyahu et al., 1989, Proc. Natl. Acad. Sci. USA 86, 8763–8767; Finlay et al., 1989, Cell 57, 1083–1093) and have been shown to relate to its capacity to function as a sequence-specific transcription factor (Pietenpol et al., 1994, Proc. Natl. Acad. Sci. USA 91, 1998–2002; Crook et al., 1994, Cell 79, 817–827), and to interact with key cellular proteins. The critical role served by p53 in these diverse physiological processes necessitates that p53 activity be subject to stringent multi-level regulation. One crucial level of regulation involves the MDM2 protein whose direct interaction with p53 blocks p53-mediated transactivation (Chen et al., 1995, Mol. Med 1, 141–142) and targets the p53 protein for rapid degradation (Levine, 1997, Cell 88, 323–331; Kubbutat et al., 1997, Nature 387, 299–303; Haupt et al., 1997, Nature 387, 296–299). MDM2 itself has been shown to be amplified in primary tumors (Oliner et al., 1992, Nature 362, 857–860), to act as an immortalizing oncogene in cell culture (Finlay, 1993, Molecular & Cellular Biology 13, 301–306), and to directly repress basal transcription (Thut et al., 1997, Genes Devel. 11, 1974–1986).

In human cancers, disruption of the RB pathway can result from inactivation of RB itself through gene mutation/deletion, viral sequestration or hyperphosphorylation (Weinberg, 1995, Cell 81, 323–330), or through disregulation of the components controlling the degree of RB phosphorylation. The latter can take place through activating mutations in the G1 specific Cyclin-Dependent Kinase 4 (CDK4) catalytic unit, up-regulation of D-type cyclin levels, and/or elimination of INK4s (for INhibitors of Cyclin-Dependent Kinase 4) (Sherr, 1996, Science 274, 1672–1676). The products of INK4 family genes have been shown to bind to CDK4 and inhibit CDK4-directed phosphorylation of Rb (Quelle, et al., 1995a, Oncogene 11, 635–645; Serrano et al., 1993, Nature 366, 704–707), thereby blocking exit from the G1 phase of the cell cycle (Sherr, 1996, Science 274, 1672–1676). One member of the INK4 family, INK4a, has been shown to exhibit loss of function in a wide spectrum of tumor types; this pathogenetic event appears to be exceeded in frequency only by p53 inactivation. The basis for the prominence of INK4a, as opposed to other members of the INK4 family, in tumor suppression is not fully understood but may relate to its unusual capacity to encode two distinct proteins—the cyclin-dependent kinase inhibitor, $p16^{INK4a}$, and a novel protein of unknown function, $p19^{ARF}$. This special feature of INK4a results from a unique gene organization in which the two INK4a gene products are encoded by different first exons and alternative reading frames residing in a common second exon. The fact that both gene products are often eliminated or mutated in many cancers has raised questions regarding their relative contributions to INK4a-mediated tumor suppression.

Compelling support for $p16^{INK4a}$ as a critical target of tumorigenesis includes germline mutations/deletions exclusively affecting the $p16^{INK4a}$ ORF in melanoma-prone kindreds and a tumor-associated CDK4 mutation rendering this kinase insensitive to $p16^{INK4a}$ inhibition (Zuo et al., 1996, Nature Genet. 12, 97–99). With regard to $p19^{ARF}$, although direct evidence linking loss of $p19^{ARF}$ function with human tumorigenesis has been lacking, many INK4a mutations/deletions map to the exon 2 region that is shared by $p19^{ARF}$ and a $p19^{ARF}$-specific knockout leads to spontaneous tumor formation in mice (Kamijo et al., 1997a, Cell 91, 649–659).

Some clues addressing $p19^{ARF}$'s mechanism of action have been provided by the requirement for p53 in $p19^{ARF}$-induced G1 arrest and by an absence of p53 mutations in post-crisis $p19^{ARF}$−/− MEF cultures (Kamijo et al., 1997a, Cell 91, 649–659) and in RAS-induced melanomas arising in the INK4a null mice (Chin et al., 1997, Genes and Development 11, 2822–2834). Additionally, studies reported here suggest that $p19^{ARF}$ requires p53 function to suppress cellular transformation. All of these observations have led to the intriguing possibility that the INK4a gene is linked not only to the Rb pathway through $p16^{INK4a}$ but also to the p53 pathway through $p19^{ARF}$.

The present invention describes the determination of the function of the novel protein $p19^{ARF}$. The inventors have determined that the novel $p19^{ARF}$ protein acts as a suppressor of oncogenic transformation. The inventors specifically ascertained that $p19^{ARF}$ engages the p53 pathway through physical interactions with the MDM2 oncoprotein. $p19^{ARF}$ specifically inhibits the oncogenic actions of MDM2, blocks MDM2-induced degradation of p53, and enhances p53-dependent transactivation. The inventors additionally demonstrated that loss of INK4a attenuates apoptosis brought about by Rb deficiency. These studies provide physical and mechanistic insight fortifying INK4a's position at the nexus of the two most important tumor suppressor pathways governing the development of neoplasia, and provide an explanation for the frequent involvement of INK4a in tumorigenesis.

SUMMARY OF THE INVENTION

The present invention provides a novel method of inhibiting the growth of tumor cells based upon the discovery that p19$^{ARF}$ acts as a suppressor of oncogenic transformation by binding to the MDM2 oncoprotein and blocking MDM2's ability to target associated proteins, such as p53 and Rb, for proteosomal degradation.

The present invention specifically provides a method of inhibiting the growth of a tumor cell by introducing to the cell an effective amount of p19$^{ARF}$ or a mimetic thereof, and p53 to inhibit the growth of the tumor cell.

The present invention further provides a pharmaceutical composition comprising p19$^{ARF}$ in the form of a protein, a nucleic acid encoding p19$^{ARF}$, a nucleic acid encoding p19$^{ARF}$ contained in a vector, or a mimetic thereof. Also provided is a pharmaceutical composition comprising p19$^{ARF}$ in the form of a protein, a nucleic acid encoding p19$^{ARF}$, a nucleic acid encoding p19$^{ARF}$ contained in a vector, or a mimetic thereof, and p53.

Additional objects of the present invention will be apparent from the description which follows.

BRIEF DESCRIPTION OF THE FIGURES

FIGS. 1A and 1B set forth an anti-oncogenic profile of the mouse p16$^{Ink4a}$ and p19$^{ARF}$ expression constructs in Myc/RAS versus E1a/RAS cotransformation assays. FIG. 1A shows a histogram of a representative REF cotransformation assay showing the average number of foci per 10 cm plate following cotransfections with mouse c-myc, H-RAS$^{val12}$ and 2 µg of the various expression constructs listed above each bar. FIG. 1B shows the same experimental design as described in FIG. 1A except that each plate was cotransfected with 2 µg E1a, H-RAS$^{val12}$, and the various expression constructs listed. In this particular experiment, the p16$^{Ink4a}$ transfection point exhibited an artificially low number of foci relative to the empty vector. Although this decline is not statistically significant, in all other experiments the addition of human or mouse p16$^{Ink4a}$ has little or no inhibition against E1a/RAS transformation, similar to previous studies (Serrano M., et al., Science 267, 249–252 (1995)). Support for the lack of an effect also derives from the lack of additional suppression by p16$^{Ink4a}$ in the p16$^{Ink4a}$+p19$^{ARF}$ transfection point compared to p19$^{ARF}$ alone. The general cyclin-dependent kinase inhibitor p21$^{CIP1}$ served as a positive control for an inhibitory agent acting in G1 and G2M phases of the cell cycle.

FIGS. 2A–2C demonstrate the anti-oncogenic activity of p19$^{ARF}$ in relation to p53. FIG. 2A sets forth a histogram of a representative REF cotransformation assay showing the average number of foci per 10 cm plate following cotransfections with 2 µg each of mouse Tag, H-RAS$^{val12}$ and empty vector or p19$^{ARF}$. FIG. 2B is similar to A except that p53 KH213 and H-RAS$^{val12}$ were used to generate foci. FIG. 2C shows a Myc/RAS cotransformation assay conducted with MEFs homozygous null for p53. The bars represent the % foci generated in the presence of 2 µg p16$^{Ink4a}$ or p19$^{ARF}$ relative to control plates receiving 2 µg c-myc, 2 µg RAS and 2 µg empty vector. In the MEF assays, clear countable Myc/RAS foci are not generated in wildtype MEF cultures, thus a direct comparison to MEFs wildtype for p53 is not possible. However, INK4a–/–MEF cultures that are wildtype for p53 and do allow for readable foci counts (Serrano, M., et al., Cell 85, 27–37 (1996)) exhibited a 4-fold reduction with the addition of p19$^{ARF}$ to Myc/RAS cotransfections (data not shown), a result comparable to that obtained with REF cultures.

FIGS. 3A and 3B represent the p19$^{ARF}$ MDM2 interaction in vivo. FIG. 3A shows an IP-Western analysis of 293T cells transfected with the indicated expression constructs above the panel. The α-MDM2 (lanes 2 and 3) and α-FLAG (lanes 4–6) immunoprecipitates were Western-blotted and assayed with an α-MDM2 antibody. FIG. 3B sets forth an IP-Wextern analysis of untransfected 3T3DM employing the antibody listed below the panel (NI, nonimmune; H.C., heavy chain) and blotted with α-MDM2 antibody.

FIGS. 4A–4I demonstrate the effect of p19$^{ARF}$ on p53-mediated apoptosis and transactivation. Representative sections of age-matched lenses showing morphology by H&E stain, proliferation by BrdU incorporation, and apoptosis by TUNEL assay in E14.5 wildtype (FIG. 4A, FIG. 4D and FIG. 4G), Rb–/– (FIG. 4B, FIG. 4E and FIG. 4H) and Rb–/–, INK4a–/– (FIG. 4C, FIG. 4F and FIG. 4I) lenses are shown. The lenses are oriented with the anterior epithelium (ep) facing the lower left corner and the lens fiber region (lf) facing the upper right corner. The arrows in FIG. 4H and FIG. 4I point to TUNEL-positive nuclei.

FIGS. 5A and 5B. FIG. 5A shows a quantitative comparison of apoptosis nuclei relative to the total number of lens fiber nuclei in E13.5 and E14.5 Rb–/– (solid) and Rb–/–, INK4a–/– lenses (striped). FIG. 5B shows a CAT reporter quantitation following transfection of the indicated plasmids containing the CAT gene driven by p53-responsive (PG13) or non-responsive (MG13) promoters. Each transfection point received wildtype p53 and the indicated amount of p19$^{ARF}$ construct. Basal activity of the PG13 CAT reporter was arbitrarily assigned a value of 1.0.

FIG. 6A demonstrates the cooperative effects of the mouse p16$^{Ink4a}$ and p19$^{ARF}$ expression constructs in Myc/RAS cotransformation assays. Histogram of a representative REF cotransformation assay showing the average number of foci per 10 cm plate following cotransfections with 2 µg mouse c-myc, H-RAS$^{val12}$ and the various expression constructs listed above the error bars. FIG. 6B sets forth the distinct actions of p16$^{Ink4a}$ and p19$^{ARF}$ expression constructs in E1a/RAS cotransformation assays. The same experimental design as described in FIG. 6A except that each plate was co-transfected with 2 µg E1a, H-RAS$^{val12}$, and the various expression constructs listed. In this particular experiment, the p16$^{Ink4a}$ transfection point exhibited an usually low number of foci relative to the empty vector. Although this decline is not statistically significant, in all other experiments the addition of mouse p16$^{Ink4a}$ had no inhibition against E1a/RAS transformation, similar to previous studies with the human p16$^{Ink4a}$ (Serrano et al., 1995). Support for the lack of an effect also derives from the lack of additional suppression by p16$^{Ink4a}$ in the p16$^{Ink4a}$+ p19$^{ARF}$ transfection point compared to p19$^{ARF}$ alone. The general cyclin-dependent kinase inhibitor p21$^{CIP1}$ served as a positive control for an inhibitory agent acting downstream of Rb. FIG. 6C shows anti-oncogenic activity of p19$^{ARF}$ in T-Ag/RAS or dominant negative p53/RAS REF cotransformation assays. On the left, histogram of a representative REF cotransformation assay showing the average number of foci per 10 cm plate following cotransfections with 2 μg each of T-Ag, H-RAS$^{val12}$ and empty vector or p19$^{ARF}$. On the right, histogram showing the average number of foci per 10 cm plate following cotransfections with 2 μg each of p53 KH215 (encoding a dominant negative mutant p53) and H-RAS$^{val12}$ with or without p19$^{ARF}$. FIG. 6D sets forth anti-oncogenic activity of p19$^{ARF}$ in Myc/RAS MEF cotransformation assays. The early passage MEFs used for each experiment were either null for INK4a (left panel) or null for both INK4a and p53 (right panel). The bars represent the number of foci generated in the presence of p19$^{ARF}$ relative to control plates receiving 2 μg c-myc, 2 μg RAS and 2 μg empty vector. These assays were performed on an Ink4a null background because wild-type MEFs do not give clear, countable foci in Myc/RAS cotransformation assays.

FIGS. 7A–7F set forth an analysis of the p19$^{ARF}$ complex in vivo. FIG. 7A shows a co-immunoprecipitation assay with anti-p53 antibody following transfection of the indicated expression constructs into 293T cells. Western blots were probed with anti-FLAG antibody (HC heavy chain, LC light chain) (15% SDS-PAGE). FIG. 7B sets forth 293T cells transfected with the indicated expression constructs were metabolically labeled, and immunoprecipitations using anti-FLAG (lanes 5–8) or anti-MDM-2 (lanes 9–12) antibodies were performed. Precipitated proteins were analyzed on a 4–15% SDS-PAGE gradient gel. FIG. 7C depicts an immunoprecipitation-Western blot analysis of 293T lysates following transfection with the indicated expression constructs. The lysates were immunoprecipitated with the antibodies indicated below the lanes and the blots were probed with an anti-MDM2 antibody (8% SDS-PAGE). FIG. 7D is the same as FIG. 7C except that lysates were derived from untransfected 3T3DM cells which express high levels of MDM2, p19$^{ARF}$ and p53. The asterisk marks the MDM2 forms that do not interact with p53. The anti-p19$^{ARF}$ is a rabbit polyclonal p19$^{ARF}$ antisera and is compared with non-immune rabbit serum (NRS) (8% SDS-PAGE). FIG. 7E is the same as FIG. 7C except that SAOS2 cells were used. FIG. 7F sets forth a confocal microscopic analysis of MDM2 and p19$^{ARF}$ protein distribution in 293T nuclei. The yellow signal indicates co-localization of the two proteins. A staining pattern similar to that observed for p19$^{FLAG}$ in 293T cells has been observed previously for p19$^{ARF}$ (Quelle et al., 1995b, Cell 83, 993–1000), supporting that this apparent nucleolar localization pattern is not an artifact of over-expression or epitope tagging.

FIGS. 8A and 8B show the localization of p19$^{ARF}$ interaction region of MDM2. FIG. 8A sets forth a graphic representation of the full length MDM2 protein (top) and MDM2 deletion mutants. The known structural motifs and functional domains of MDM2 are indicated. With regard to the 1–58 mutant, previous studies have determined that these sequences are essential for MDM2 interaction with p53 (Oliner et al., 1993, Nature 362; 857–860; Momand et al., 1992, Cell 69, 1237–1245; Kussie et al., 1996, Science 274, 948–953). FIG. 8B sets forth a western blot analysis of lysates (lanes 2, 4, 6, 8, 10, 12, 14) and of anti-FLAG immunoprecipitates (lanes 1, 3, 5, 7, 9, 11, 13, 15) following transient transfection of the indicated expression constructs into 293T cells (lanes 1–7, 10–13) or SAOS2 cells (lanes 8–9, 14–15). Asterisks denote the MDM2 band of interest in each immunoprecipitate. Lanes containing lysate demonstrate that the transfected MDM2 and its mutant derivatives are expressed at high levels. Note the absence of an MDM2 band in the anti-FLAG precipitates after transfection of 155–491 and p19$^{FLAG}$ The nuclear localization of each mutant protein was confirmed by in situ immunohistochemistry (data not shown). The Western blots were probed with anti-MDM2 monoclonal antibody directed to an epitope (aa 26–168) present within all of the MDM2 proteins used in this assay. 8% SDS-PAGE (lanes 1–9). 14% SDS-PAGE (lanes 10–15). HC, heavy chain. LC, light chain.

FIGS. 9A–9D show the effect of p19$^{ARF}$ on MDM2-related functions. FIG. 9A sets forth a representative MDM2/RAS cotransformation experiment comparing transformed foci counts in MDM2/RAS cotransfections receiving either empty vector, p16$^{INK4a}$ or p19$^{ARF}$. FIG. 9B: Top panel: Western blot analysis of HeLa cell lysates probed with anti-p53 antibody (Ab-1 Calbiochem) following transfection of the indicated expression constructs. Middle panel: Western blot of the same lysates probed with an anti-MDM2 antibody. Note induction of endogenous MDM2 upon transfection of p53. The very modest reduction in MDM2 levels observed upon addition of p19$^{ARF}$ (lanes 3 versus 4) is not likely to account for the p19$^{ARF}$ effect since MDM2 levels are greatly increased over those observed in the p53 alone transfections (compare lanes 4 and 2). Bottom panel: Western blot probed with anti-FLAG antibody showing a non-specific cross reacting FLAG epitope (NSFE) used as a loading control. FIG. 9C shows the higher molecular weight forms of p53 that are induced by MDM2 and thought to represent polyubiquitinated p53 targeted for proteasomal degradation. Note that there is a decrease in these bands upon addition of p19$^{ARF}$. In this particular experiment, visualization of these p53 bands is facilitated by transfection of higher amounts of p53, use of 2 different anti-p53 antibodies (DO-1 and 1801), and film over-exposure. FIG. 9D: Top panel: p53-dependent CAT reporter assays documenting the effects of p19$^{ARF}$, MDM2 or both on p53 transactivation activity. Amounts loaded are normalized for transfection efficiency. For these SAOS2 transfections, the amounts of DNA used were either 0.2 or 0.5 μg for p53 and 2 μg each for MDM2 or p19$^{ARF}$. Bottom panel: Histogram representation of p53 CAT activities as determined by PhosphorImager quantitation of signal intensities.

FIGS. 10A and 10B show the effect of INK4a deficiency on proliferation and apoptosis in the Rb-deficient lens in vivo. FIG. 10A sets forth representative sections of age-matched lenses showing morphology by H&E stain, proliferation by BrdU incorporation, and apoptosis by TUNEL assay in E14.5 wildtype (a,d,g), Rb–/– (b,e,h) and Rb–/–, INK4a–/– (c,f,i) lenses. The lenses are oriented with the anterior epithelium facing the lower left corner and the lens fiber region facing the upper right corner. TUNEL-positive nuclei are stained brown by HRP reaction. FIG. 10B: Left Panel: Quantitative comparison of S phase nuclei (BrdU-positive) relative to the total number of lens fiber nuclei in E13.5 and E14.5 Rb–/– (solid) and Rb–/–, INK4a–/– lenses (striped) (data compiled from examining 332 sections from 19 embryos). Right Panel: Quantitative comparison of apoptotic nuclei (TUNEL-positive) relative to the total number of lens fiber nuclei in E13.5 and E14.5 Rb–/– (solid) and Rb–/–,INK4a–/– lenses (striped) (data compiled from examining 174 sections from 13 embryos).

FIG. 11A sets forth a schematic of the One gene-two products-two pathways hypothesis positioning the INK4a gene along the Rb and p53 tumor suppressor pathways. FIG. 11B sets forth the proposed mechanism for p19$^{ARF}$'s enhancement of p53-related functions.

DETAILED DESCRIPTION OF THE INVENTION

Figure 1A:
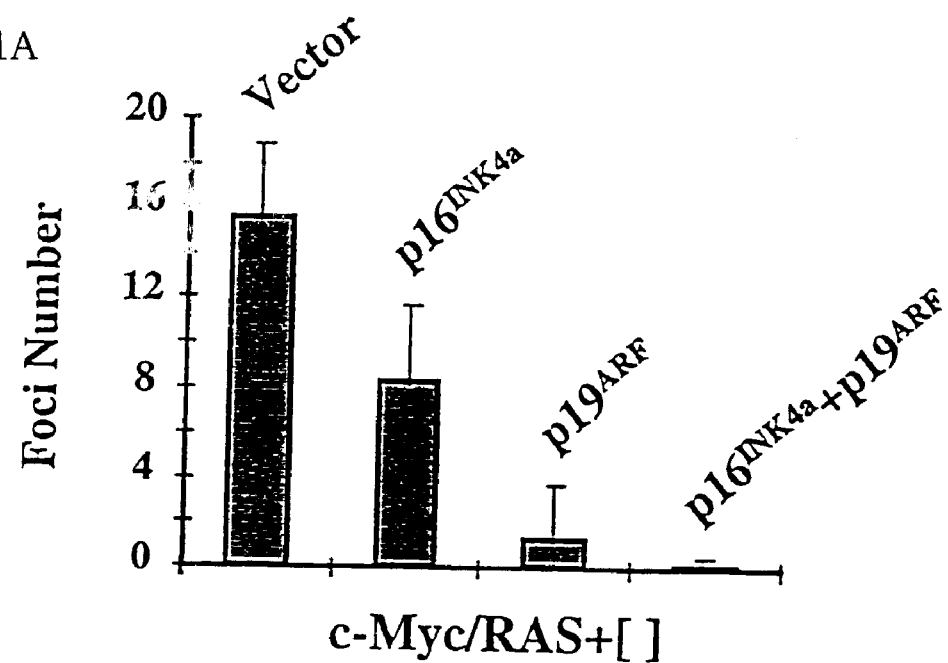
FIGS. 1A and 1B.

The present invention provides a novel method of inhibiting the growth of tumor cells. This method is based upon the important discovery that p19$^{ARF}$ acts as a suppressor of oncogenic transformation by binding to the MDM2 oncoprotein and blocking MDM2's ability to target associated proteins, such as p53 and Rb, for proteosomal degradation.

The present invention specifically provides a method of inhibiting the growth of a tumor cell by introducing to the cell an effective amount of p19$^{ARF}$ or a mimetic thereof, and p53 to inhibit the growth of the tumor cell.

The p19$^{ARF}$ and p53 proteins of the present invention may be the wild type proteins, or analogues thereof, and may be produced synthetically or recombinantly, or may be isolated from native cells. As used herein, "analogue" means functional variants of the wild type protein, and includes p19$^{ARF}$ or p53 protein isolated from mammalian sources other than human, as well as functional variants thereof.

As used herein, "mimetic" is any agent, such as a synthetic chemical or a protein, which, like p19$^{ARF}$, binds to MDM2 and blocks MDM2's ability to target an associated protein, such as p53 and Rb, for proteosomal degradation. In a specific embodiment of the invention, the mimetic prevents MDM2's ability to target p53, thereby blocking degradation of p53. p19$^{ARF}$-like mimetics may be sterochemically designed so that, based upon the protein structure and characteristics of p19$^{ARF}$, they will bind to the MDM2 protein and prevent its ability to target proteins.

Alternatively, the mimetics provided by the present invention may be nucleic acid sequences or proteins that directly bind to the amino acid sequence or the nucleic acid sequence of the MDM2 protein and thereby effect transcription or translation of the sequence, ultimately inhibiting or altering the ability of the MDM2 protein to target associated proteins, such as p53 and Rb, for proteosomal degradation. The sequences of these nucleic acids and proteins may be determined based upon the amino acid sequence or the nucleic acid sequence of MDM2 and its area of interaction with p19$^{ARF}$.

The mimetics of the present invention may comprise proteins, polypeptides, peptides, nucleic acid sequences, and small non-peptide organic molecules that have been shown to inhibit the interaction of MDM2 with p53. The nucleic acid sequences may comprise RNA, antisense RNA, double stranded RNA, RNA-DNA hybrids, double stranded DNA, nucleotides, oligonucleotides, or antisense oligonucleotides that also directly bind to or alter the ability of MDM2 to target associated proteins involved in proteosomal degradation.

Once the sequence of the mimetic is determined, the sequences may then be prepared in several ways. For example, the nucleotide sequences may be isolated from a natural source, or may be synthesized using recombinant DNA techniques. The amino acid sequences may be synthesized by methods commonly known to one skilled in the art (*Modern Techniques of Peptide and Amino Acid Analysis*, John Wiley & Sons (1981); M. Bodansky, *Principles of Peptide Synthesis*, Springer Verlag (1984)). Examples of methods that may be employed in the synthesis of the amino acids sequences, include, but are not limited to, solid phase peptide synthesis, solution method peptide synthesis, and synthesis using any of the commercially available peptide synthesizers. The amino acid sequences may contain coupling agents and protecting groups used in the synthesis of the protein sequences, and are well known to one of skill in the art.

p19$^{ARF}$ or a mimetic thereof, and p53 may be introduced to a cell as a protein, nucleic acid, or nucleic acid contained in a vector. It is to be understood that any combination of these may be used. For example, p19$^{ARF}$ or a mimetic thereof may be administered to a cell as a protein while p53 is administered to the cell as nucleic acid encoding p53, or nucleic acid encoding p53 contained in an expression vector. In addition, nucleic acid encoding p19$^{ARF}$ or a mimetic thereof, or nucleic acid encoding p19$^{ARF}$ or a mimetic thereof contained in an expression vector may be administered to a cell, while p53 is administered to the cell as a protein.

Nucleic acid encoding p19$^{ARF}$ or a mimetic thereof, and p53 and nucleic acid encoding p19$^{ARF}$ or a mimetic thereof, and p53 contained in an expression vector, may be administered to a tumor cell using many methods known to one skilled in the art. For example, nucleic acid encoding p19$^{ARF}$ or a mimetic thereof, and p53 contained in an expression vector may be introduced to a cell using gene therapy. Gene therapy comprises the introduction of a recombinant vector containing a nucleic acid sequence encoding p19$^{ARF}$, a mimetic thereof, or p53 into a cell. The recombinant vector containing DNA encoding p19$^{ARF}$, a mimetic thereof, or p53, may be introduced into the tumor cell using any number of procedures known to one skilled in the art, such as electroporation, DEAE Dextran, monocationic liposome fusion, polycationic liposome fusion, protoplast fusion, DNA coated microprojectile bombardment, by creation of an in vivo electrical field, injection with recombinant replication-defective viruses, homologous recombination, and naked DNA transfer. It is to be appreciated by one skilled in the art that any of the above methods of nucleic acid transfer may be combined. Accordingly, a stem cell which expresses p19$^{ARF}$ or a mimetic thereof, and p53 introduced therein through viral transduction, homologous recombination, or transfection is also provided by the present invention.

The recombinant vector may comprise a nucleic acid of or corresponding to at least a portion of the genome of a virus, where this portion is capable of directing the expression of a DNA sequence, and the nucleic sequence encoding a p19$^{ARF}$ or a mimetic thereof, or p53, operably linked to the viral nucleic acid and capable of being expressed as a functional gene product in the target tumor cell. The recombinant vectors may be derived from a variety of viral nucleic acids known to one skilled in the art, e.g. the genomes of HSV, adenovirus, adeno-associated virus, Semiliki Forest virus, vaccinia virus, and other viruses, including RNA and DNA viruses.

The recombinant vectors may also contain a nucleotide sequence encoding suitable regulatory elements so as to effect expression of the vector construct in a suitable host cell. As used herein, "expression" refers to the ability of the vector to transcribe the inserted DNA sequence into mRNA so that synthesis of the protein encoded by the inserted nucleic acid can occur. Those skilled in the art will appreciate that a variety of enhancers and promoters are suitable for use in the constructs of the invention, and that the constructs will contain the necessary start, termination, and control sequences for proper transcription and processing of the nucleic acid sequence encoding a protein involved in the regulation of smooth muscle tone when the recombinant vector construct is introduced into a host cell.

Vectors suitable for the expression of the nucleic sequence encoding p19$^{ARF}$ or a mimetic thereof, or p53 are well known to one skilled in the art and include pET-3d (Novagen), pProEx-1 (Life Technologies), pFastBac 1 (Life Technologies), PSFV (Life Technologies), pcDNA II (Invitrogen), pSL301 (Invitrogen), pSE280 (Invitrogen), pSE380 (Invitrogen), pSE420 (Invitrogen), pTrcHis A,B,C (Invitrogen), pRSET A,B,C (Invitrogen), pYES2 (Invitrogen), pAC360 (Invitrogen), pVL1392 and pVl1392 (Invitrogen), pCDM8 (Invitrogen), pcDNA I (Invitrogen), pcDNA I (amp) (Invitrogen), pZeoSV (Invitrogen), pcDNA 3 (Invitrogen), pRc/CMV (Invitrogen), pRc/RSV (Invitrogen), pREP4 (Invitrogen), PREP7 (Invitrogen), pREP8 (Invitrogen), pREP9 (Invitrogen), pREP10 (Invitrogen), PCEP4 (Invitrogen), pEBVHis (Invitrogen), and λPop6. Other vectors would be apparent to one skilled in the art.

Suitable promoters include, but are not limited to, constitutive promoters, tissue specific promoters, and inducible promoters. Expression of the nucleic acid sequence encoding p19$^{ARF}$ or a mimetic thereof, or p53 may be controlled and affected by the particular vector into which the nucleic acid sequence has been introduced. Some eukaryotic vectors have been engineered so that they are capable of expressing inserted nucleic acids to high levels within the target cell. Such vectors utilize one of a number of powerful promoters to direct the high level of expression. Eukaryotic vectors use promoter-enhancer sequences of viral genes, especially those of tumor viruses. This particular embodiment of the invention provides for regulation of expression of the nucleic acid sequence encoding p19$^{ARF}$. For a mimetic thereof, or p53 using inducible promoters. Non-limiting examples of inducible promoters include, but are not limited to, metallothionine promoters and mouse mammary tumor virus promoters. Depending on the vector, expression of the nucleic acid sequence encoding p19$^{ARF}$ or a mimetic thereof, or p53 would be induced in the tumor cell by the addition of a specific compound at a certain point in the growth cycle of the cell. Other examples of promoters and enhancers effective for use in the recombinant vectors include, but are not limited to, CMV (cytomegalovirus), SV40 (simian virus 40), HSV (herpes simplex virus), EBV (epstein-barr virus), retroviral, adenoviral promoters and enhancers, and tumor cell specific promoters and enhancers.

Also provided by the present invention are pharmaceutical compositions comprising the p19$^{ARF}$ protein, DNA encoding p19$^{ARF}$, or a recombinant vector encoding p19$^{ARF}$, together with a pharmaceutically or physiologically acceptable carrier. The pharmaceutical composition may additionally contain p53 in the form of a protein, nucleic acid expressing p53, or nucleic acid expressing p53 contained in a vector. The pharmaceutical composition may further comprise p16$^{Ink4a}$ in the form of a protein, nucleic acid expressing p16$^{Ink4a}$, or nucleic acid expressing p16$^{Ink4a}$ contained in a vector. Such compositions may be prepared by adding the p19$^{ARF}$ protein, nucleic acid encoding p19$^{ARF}$, or a recombinant vector encoding p19$^{ARF}$ separately or in combination with p53 protein, nucleic acid encoding p53, or a recombinant vector encoding p53 to the pharmaceutically or physiologically acceptable carrier. Suitable pharmaceutically or physiologically acceptable carriers include, but are not limited to, water containing physiologically compatible substances such as sodium chloride, glycine, and the like, having a buffered pH compatible with physiological conditions to produce an aqueous solution, and rendering said solution sterile.

Further provided by the present invention is a method of treating cancer by preventing the occurrence of and inhibiting the progression of many different types of cancers and benign proliferation disorders by administering to a subject an effective amount of p19$^{ARF}$, or a mimetic thereof, and p53 to inhibit the growth of the cancer. Non-limiting examples of cancers that can be treated using the agents provided by the present invention include melanoma, bladder carcinoma, oral carcinoma, lung carcinoma, and lymphoid neoplasms such as B-cell chronic lymphocytic leukemia, Hodgkin's and non-Hodgkin's lymphomas. Non-limiting types of benign proliferation disorders that are characterized by an abnormal proliferation of cells include benign nephrosclerosis, benign prostatic hyperplasia. Veterinary uses are also intended to be encompassed by this invention.

Administration of the pharmaceutical composition containing p19$^{ARF}$, nucleic acid encoding p19$^{ARF}$, or a mimetic thereof, along with p53, may be administered to a tumor cell of a subject by methods not limited to gene therapy, creation of an in vivo electrical field, injection with recombinant replication-defective viruses, homologous recombination, and naked DNA transfer. It is to be appreciated by one skilled in the art that any of the above methods of DNA transfer may be combined. Accordingly, a stem cell which expresses p19$^{ARF}$ or a mimetic thereof, or p53 introduced therein through viral transduction, homologous recombination, or transfection is also provided by the present invention may also be administered to a subject to inhibit growth of cells.

Administration of the pharmaceutical composition may be for either a prophylactic or therapeutic use. When provided prophylactically, the composition is provided in advance to the symptom caused by the condition afflicting the individual. When provided therapeutically, the composition is provided at, or shortly after, the onset of any symptoms of the disease. The therapeutic administration of the composition serves to attenuate the condition.

The pharmaceutical composition containing p19$^{ARF}$ protein, nucleic acid encoding p19$^{ARF}$, or nucleic acid encoding p19$^{ARF}$ contained in a vector, or a mimetic thereof, may be administered to a subject, tumor, or cell prior to, simultaneously with or subsequent to administration of p53 protein, nucleic acid encoding p53 protein, or nucleic acid encoding p53 protein contained in a vector.

For the purposes of gene transfer into a tumor cell of a subject, a recombinant vector containing nucleic acid encoding p19$^{ARF}$ or a mimetic thereof, or p53 may be combined with a sterile aqueous solution which is preferably isotonic with the blood of the recipient Such formulations may be prepared by suspending the recombinant vector in water containing physiologically compatible substances such as sodium chloride, glycine, and the like, and having buffered pH compatible with physiological conditions to produce an aqueous solution, and rendering such solution sterile. In a preferred embodiment of the invention, the recombinant vector is combined with a 20–25% sucrose in saline solution in preparation for introduction into a smooth muscle cell.

The amounts of p19$^{ARF}$, nucleic acid encoding p19$^{ARF}$, or nucleic acid encoding p19$^{ARF}$ contained in a vector, or a mimetic thereof, and p53 are in amounts sufficient to inhibit the growth of a tumor cell. However, the exact dosage will depend on such factors as the purpose of administration, the mode of administration, the size of the tumor or cancerous tissue, the stage of progression of the disease, and the efficacy of the composition, as well as the individual pharmacokinetic parameters of the subject. One of skill in the art will know the parameters to evaluate the response of the individual to the composition containing and establish the dosage based on those parameters. Such therapies may be administered as often as necessary and for the period of time as judged necessary by the treating physician.

The present invention is described in the following Experimental Details Section which is set forth to aid in the understanding of the invention, and should not be construed to limit in any way the scope of the invention as defined in the claims which follow thereafter.

Experimental Details Section

I. Materials and Methods

Expression Constructs and REF Cooperation Assays. Expression constructs encoding mouse p16$^{Ink4a}$ and p19$^{ARF}$ were generated by placing the complete ORFs derived from their respective cDNAs (Schreiber-Agus et al., 1994, Oncogene 9, 3167–3177) in the sense orientation relative to two tandemly repeated Moloney murine leukemia virus (MuLV) long terminal repeats in the pVNic vector (Schreiber-Agus et al., 1997, Cell 1995. March 10. 80, 777–786). Expression constructs for c-myc, mutant H-RAS, and E1a have all been described previously (Schreiber-Agus et al., 1997, Cell 1995. March 10. 80, 777–786) and the CMV-driven expression construct encoding the KH215 dominant-negative mutant form of p53 (Gruis et al., 1995, Am. J. Pathol. 146, 1199–1206) has been described previously. To perform the rat embryo fibroblast (REF) cooperation assays, early passage cultures of REFs were prepared and cotransfected as described previously (Schreiber-Agus et al., 1997, Cell 1995. March 10. 80, 777–786) with DNA mixtures containing 2 µg each of the relevant expression constructs plus the corresponding amount of carrier DNA, for a total of 30 µg DNA. At 9 to 12 days post-transfection, foci were scored visually and confirmed by microscopic examination to be transformed morphologically. For the MEF assays, early passage MEFs were prepared from day 13.5 embryos minced and seeded into 10 cm plates. The following day cells were split 1:3 and frozen upon reaching confluency (~24 hours). MEFs were thawed and transfected according to the REF assay protocol.

Protein analysis. For confocal analysis, 293T or 3T3DM cells were seeded on gelatin coated glass cover slips at a density of 130,000 cells per 2 cm well. Twenty 24 hrs later, the cells were transfected with 3 µg each of FLAG-tagged p19$^{ARF}$ and human MDM2 expression constructs using Lipofectamine (Gibco BRL). Forty-eight hours post transfection, cells were fixed in 2% paraformaldehyde for 10 min, washed in PBS, permeablized in 1% Triton X-100 for 10 min, blocked with 3% milk in PBS for 30 min, and incubated in primary antibody diluted in blocking solution overnight at 4° C. For FLAG-tagged p19$^{ARF}$, M2 antibody (Kodak) was used at a concentration of 5 µg/ml. Anti-MDM-2 Ab-1 (Calbiochem) was diluted 1:10. Following this incubation, cells were washed in PBS and incubated in secondary Ab for 1 hour. The secondary antibodies (Southern Biotechnology) were anti-IgG2a-Texas Red for FLAG and anti-IgG1-FITC for MDM2. All incubations except for primary antibody were at RT. Finally, cells were washed, and cover slips were mounted in 1:1 glycerol: PBS for viewing on a Bio-Rad MR600 laser scanning confocal microscope.

Figure 3A:
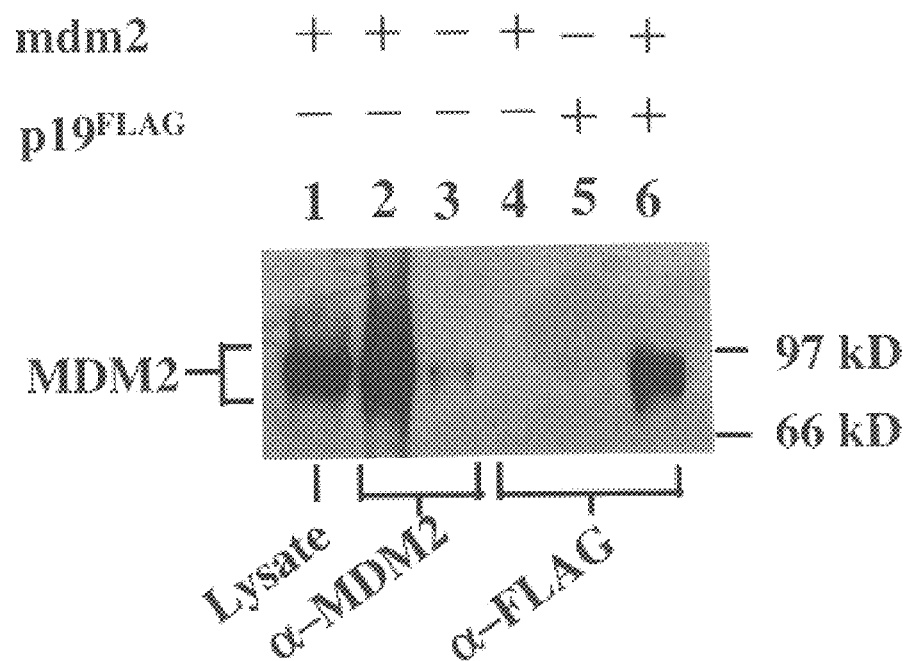
FIGS. 3A and 3B.
Figure 3B:
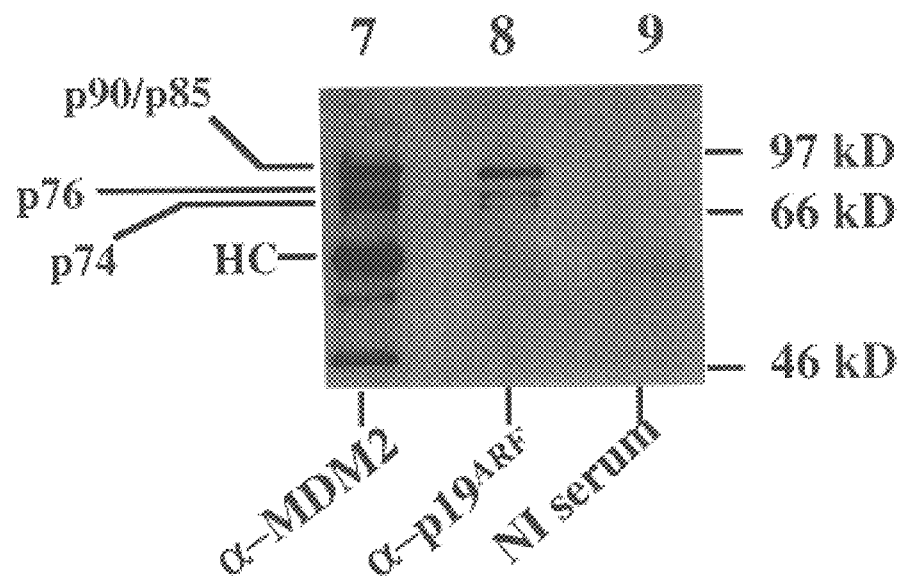

For immunoprecipitations, subconfluent 293T cells were transfected with 3 µg each of the appropriate expression constructs shown in FIG. 3, and 80 µg of Lipofectamine reagent (Gibco BRL). Immunoprecipitations under low-stringency conditions were performed (Schreiber-Agus N., et al., Cell 80, 777–786 (1995)) using anti-FLAG M2 (Kodak) and anti-MDM-2 Ab-1 (Calbiochem) antibodies. For p19$^{ARF}$, the FLAG epitope was introduced by PCR. The human-Mdm-2 expression construct was provided by Arnold Levine (Princeton) Untransfected 3T3-DM cells were lysed in a low stringency buffer as above. 1.6 mg protein was immunoprecipitated using 150 µl anti-MDM2 (2A10) (Olson D C., et al., Oncogene 8, 2353–2360 (1993)) and protein G or anti-p19$^{ARF}$ (4 µl) with protein A for 1 hour. Western blots were probed with 2A10 1:100 to detect endogenous Mdm-2. The p19$^{ARF}$ antibodies were provided by Charles Sherr (St. Judes).

Figures 4A, 4B, 4C, 4D, 4E, 4F, 4G, 4H, 4I:
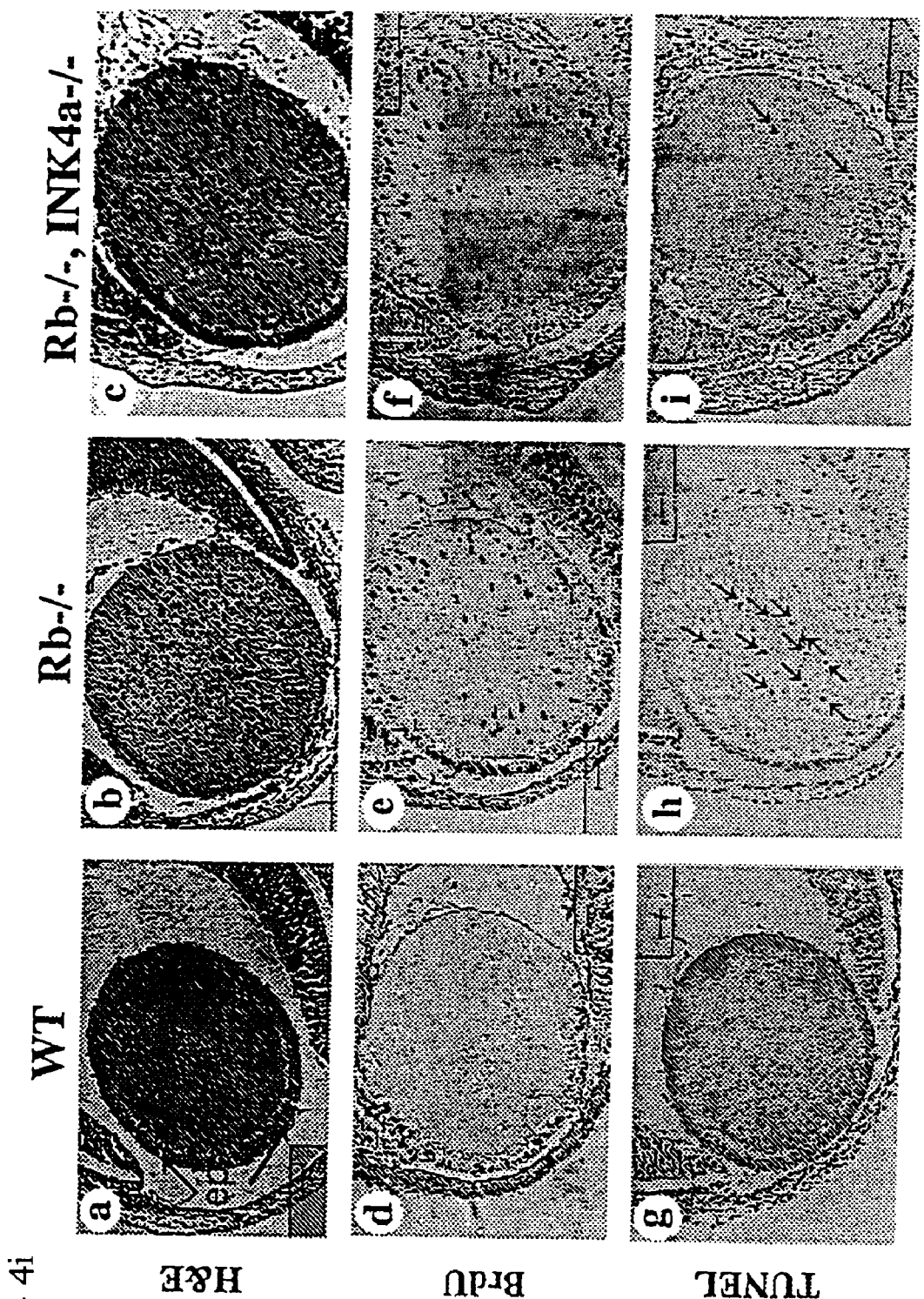
FIGS. 4A–4I.
Figure 6A:
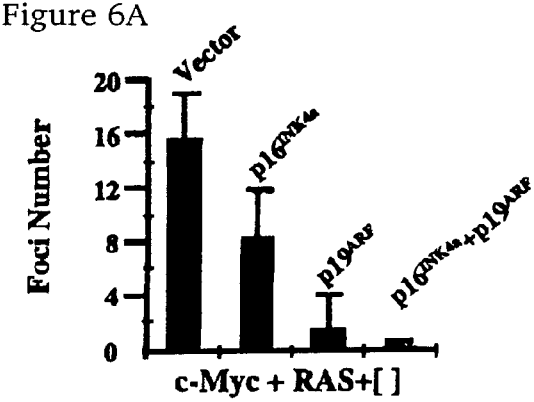
FIGS. 6A–6D.
Figure 6B:
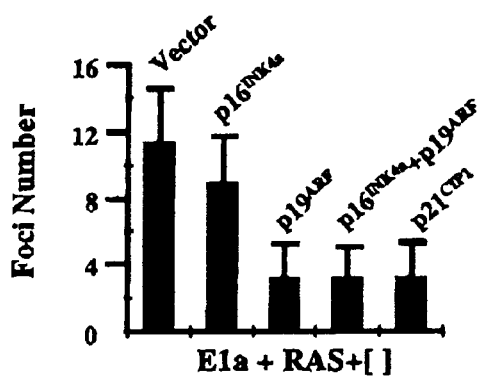
Figure 6C:
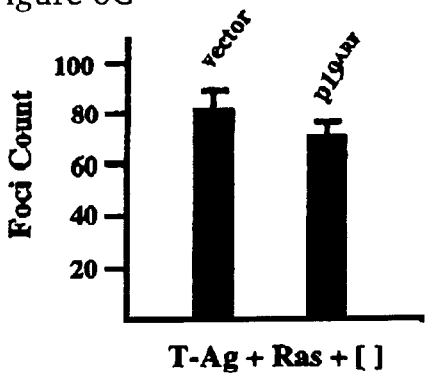
Figure 6C:
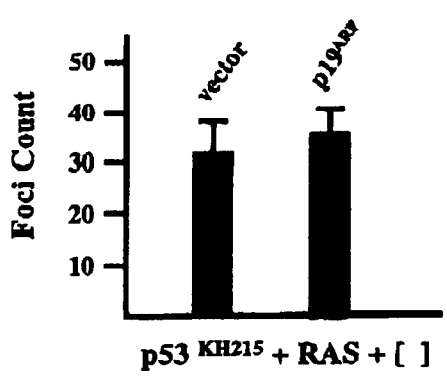
Figure 7A:
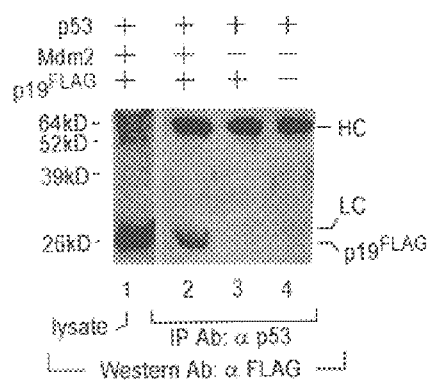
FIGS. 7A–7F.
Figure 7B:
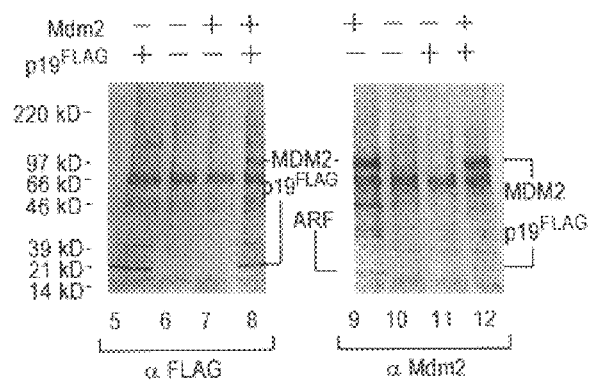
Figure 7C:
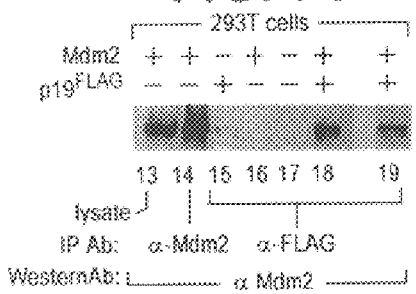
Figure 7D:
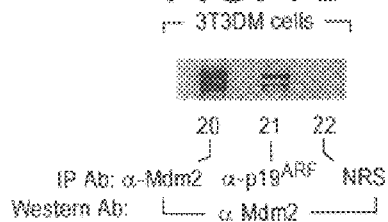
Figure 7E:
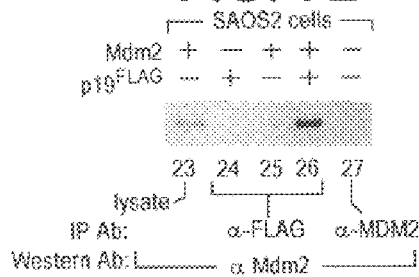
Figure 7F:
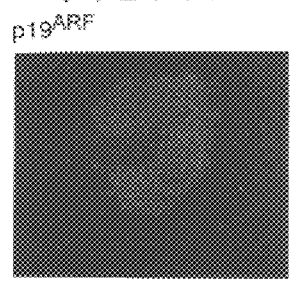
Figure 7F:
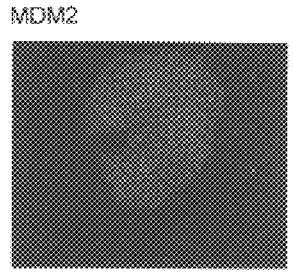
Figure 7F:
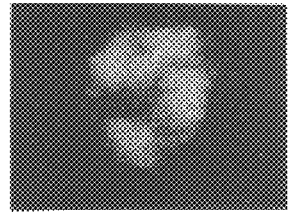
Figures 8A, 8B:
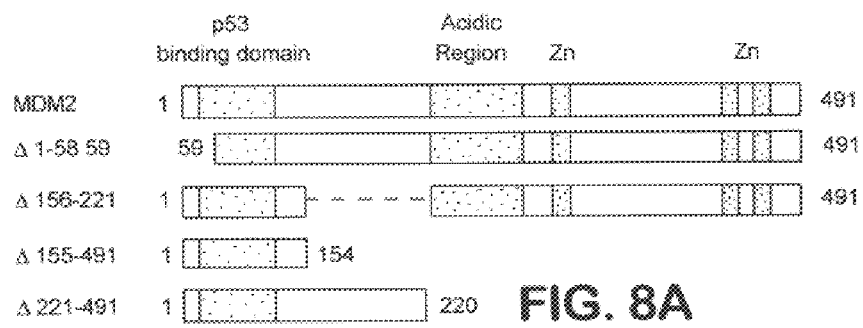
FIGS. 8A and 8B.

For the results set forth in FIGS. 6–10, 293T cells (1.4×10$^6$ per 10 cm plate in DME supplemented with 10% fetal bovine serum, glutamine and antibiotics) were transfected under serum and antibiotic free conditions with 3 µg each of the appropriate expression constructs shown in FIGS. 7 and 8, and 80 µg of Lipofectamine reagent (Gibco BRL). For FIG. 7B, cells were metabolically labeled using the EXPRESS $^{35}$S protein-labeling mix (Dupont-NEN) for 7 hours before collection. Immunoprecipitations under low-stringency conditions (1% NP-40, 10% glycerol, 10 mM NaF, 50 mM-glycerophosphate, protease inhibitors in PBS) were performed as described previously (Schreiber-Agus et al., 1997) using anti-p53 Ab-6 conjugated beads (Calbiochem), anti-FLAG M2 (Kodak) and anti-HDM-2 Ab-1 (Calbiochem) antibodies. For high-stringency immunoprecipitations, RIPA buffer (150 mM NaCl, 1% NP-40, 0.5% deoxycholate, 0.1% SDS, and 50 mM Tris) was used. To construct the FLAG epitope-tagged p19$^{ARF}$ construct, PCR was used to fuse in-frame FLAG epitope sequences at the 3' end of the p19$^{ARF}$ ORF and the sequence-verified PCR product was cloned into the pcDNA (Invitrogen) expression vector. The CMV driven human MDM2 expression construct (pCHDM1A) was provided by Arnold Levine (Princeton). The MDM2 mutant, 156–221, was created by standard PCR and utilization of internal restriction enzyme sites. Specifically, an XbaI site just 5' to bases encoding amino acid 155 was ligated in-frame to a sequence-verified PCR-generated fragment containing the 5' engineered XbaI site and beginning with amino acid residue 221 (the oligomers used are 5'-CGCCATCTAGACCGGATCTTGATGCTGGT-3' (SEQ ID NO:1) and 5'-CGAAGGGCCCAACATCTG-3' (SEQ ID NO:2)). The 3' end of this PCR fragment was fused in-frame with the remainder of the MDM2 ORF via a unique ApaI site. The final ligation was performed in the parental pCHDM1A vector in order to reconstitute the MDM2 ORF minus sequences encoding amino acids 156 to 221. SAOS2 cells (5×10$^6$ per 10 cm plate in DME supplemented with 10% fetal bovine serum, 5% calf serum, glutamine and antibiotics) were transfected by a modified calcium phosphate method as for the CAT assays (see below), and then processed as for 293Ts under low stringency conditions. Untransfected 3T3DM cells were lysed in a low stringency buffer as above. 1.6 mg of protein was immunoprecipitated using 150 µl anti-MDM-2 (2A10) (Olson et al., 1993) and protein G agarose or anti p19$^{ARF}$ (4 µl) with protein A agarose for 1 hour. Western blots were probed with 2A10 1:100 to detect endogenous MDM-2. The anti-p19$^{ARF}$ antibodies were provided by Charles Sherr (St. Judes) . For p53 degradation studies, 6×10$^5$ HeLa cells or H1299 cells maintained in DME supplemented with 10% fetal calf serum and antibiotics, or 5×10$^6$ SAOS2 cells maintained as for CAT assay were transfected by the calcium phosphate method, with 2 µg pC53SN3 (R. Tjian), 5 µg Mdm2, and/or 5 µg p19$^{FLAG}$ and harvested in RIPA buffer 24 hours after transfection. Western blots were probed with anti-p53 Ab-1 (FIG. 4B), or a mixture of monoclonal p53 antibodies DO-1 and 1801 (Santa Cruz) all at 1:100 dilution (FIG. 4C). For confocal analysis, 293T cells were seeded on gelatin coated glass cover slips at a density of 130,000 cells per 2 cm well. Twenty-four hours after seeding, the cells were transfected with FLAG-tagged p19$^{ARF}$ and human MDM-2 constructs as above Forty-eight hours post transfection, cells were fixed in 2% paraformaldehyde for 10 minutes, washed in PBS, permeablized in 1% Triton X-100 for 10 minutes, blocked with 3% milk in PBS for 30 minutes, and incubated in primary antibody diluted in blocking solution overnight at 4° C. For FLAG-tagged p19$^{ARF}$, M2 antibody, (Kodak) was used at a concentration of 5 g/ml. Anti MDM-2 Ab-1 (Calbiochem) was diluted 1:10. Following this incubation, cells were washed in PBS and incubated in secondary Ab for 1 hour. The secondary antibodies (Southern Biotechnology) were anti-IgG2a-Texas Red for FLAG and anti-IgG1-FITC for MDM-2. All incubations except for primary antibody were at room temperature. Finally, cells were washed, and cover slips were mounted in 1:1 glycerol:PBS for viewing on a Bio-RAD MR600 laser scanning confocal microscope.

TUNEL and BrdU assays. TUNEL and BrdU incorporation assays were performed as described elsewhere (Morgenbesser et al., 1994) on 3 $\mu$M paraffin-embedded lens sections prepared as described elsewhere (Morgenbesser et al., 1994).

CAT reporter assays. Cultures of 293T cells were grown in DME 10% plus fetal calf serum to 50% confluence in 10 cm (Gottlieb T M., et al., *Biochimica et Biophysica Acta.* 1287, 77–102 (1996)) tissue culture dishes and transfected by the lipofectamine (BRL) method according the manufacturer's instructions. Cells were harvested 48 hours post transfection and CAT reporter activity was assayed by acetylation of $^{14}$C-labeled chloramphenicol as reported previously (Gorman C M., et al., *Mol. Cell. Biol.* 2, 1044–1051 (1982)) except that the extracts were incubated at 37° C. for 10 min, the samples were resuspended in 20 $\mu$l of ethyl acetate, and the quantities of protein assayed for CAT were approximately 50 $\mu$g per point. Transfection efficiencies were determined by addition of 2 $\mu$g of human growth hormone plasmid to each transfection point and assaying the media for human growth hormone by radioimmunoassay (Nichols Institute) just before cell lysis. Signal were quantitated using PhosphorQuant software. The LTRp53cG(ala) expression construct encodes the wildtype human p53 protein (Eliyahu D., et al., *Proc. Natl. Acad. Sci. USA* 86, 8763–8767 (1989)). The reporter constructs, detailed elsewhere (Kern S E., et al., *Science* 256, 827–830 (1992)), were the PG13-CAT construct bearing a promoter with multiple copies of the p53 consensus binding site, and the MG-CAT in which these p53 binding sites are replaced by nonspecific sequences.

Cultures of SAOS2 cells were maintained as above and transfected by calcium phosphate using the same amounts of DNA as in p53 degradation studies and immunoprecipitation assays, plus 2.5 g PG13CAT, with DMSO shock, 5 hours after addition of the precipitate (Brown et al., 1993, Mol. Cell. Biol. 13, 6849–6857). Cells were harvested 48 hours post shocking and CAT reporter activity was assayed by acetylation of $^{14}$C-labeled chloramphenicol as reported previously (Gorman et al., 1982, Mol. Cell. Biol. 2, 1044–1051) except that the extracts were incubated at 37° C. for 45 min, the samples were resuspended in 20 $\mu$l of ethyl acetate, and the quantities of protein assayed for CAT were approximately 30% g per point. Transfection efficiencies were determined by addition of 2 $\mu$g of human growth hormone plasmid to each transfection point and assaying the media for human growth hormone by radioimmunoassay (Nichols Institute) just before cell lysis. Signal was quantitated using PhosphorQuant software.

II. Results

Two preliminary observations made in the INK4a knockout model suggested that p19$^{ARF}$ may function as a tumor suppresser protein. First, the re-introduction of either p16$^{INK4a}$ or p19$^{ARF}$ into INK4a−/−fibrosarcoma cell lines resulted in suppression of tumorigenic growth in SCID mice (data not shown). Second, molecular analysis of tumors arising in INK4a+/− mice revealed a high incidence of deletion (rather than mutation) of the remaining functional allele (data now shown). One interpretation of this homozygous codeletion is that it reflects a more efficient genetic strategy to eliminate both INK4a gene products since classically loss of tumor suppressor gene function presents with deletion of one allele followed by inactivating point mutation on the second allele (Serrano, M., et al., *Cell* 85, 27–37 (1996); Cordon-Cardo C., *Am. J. Pathol.* 147, 545–560 (1995)). These observations, along with the previously reported cell cycle-arrest activity of p19$^{ARF}$ in addition to p16$^{INK4a}$ (Serrano M., et al., *Science* 267, 249–252 (1995); Quelle D E., et al., *Cell* 83, 993–1000 (1995); Koh J., et al., *Nature* 375, 506–510 (1995)), prompted a detailed assessment of the biological activities of p19$^{ARF}$ in normal and neoplastic cells.

p19$^{ARF}$ is a potent suppressor of oncogenic transformation of primary rodent cells. The anti-oncogenic potency of each ink4a gene product was tested in the rat embryo fibroblast (REF) cotransformation assay (Land H., et al., *Nature* 304, 596–602 (1983)). In this highly quantitative assay, a comparison of the candidate suppressor's activity against various oncogene combinations, such as Myc/RAS, E1a/RAS or SV40 Large T Antigen ((TAG)/RAS, can provide a measure of its antioncogenic activity as well as yield mechanistic insight into how this activity relates to the Rb and p53 pathways.

Figure 1B:
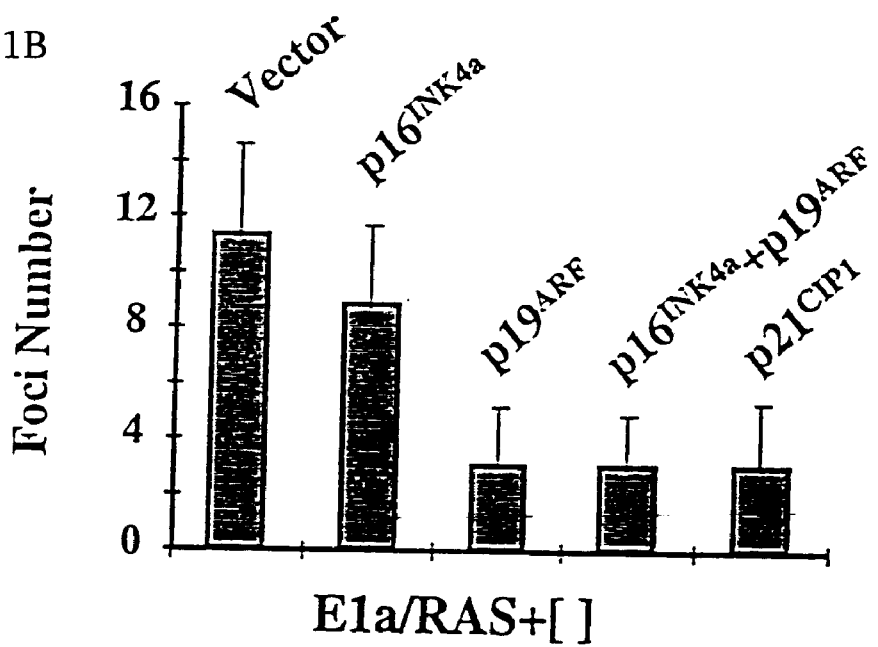

The degree of inhibition of E1a/RAS-versus Myc/RAS-induced foci formation by p19$^{ARF}$, p16$^{Ink4a}$, or both was compared in a parallel series of cotransfections; the results of a representative cotransfection experiment are shown in FIG. 1. The inventors have observed previously that human p16$^{Ink4a}$ can inhibit transformation by c-myc/RAS but not E1a/RAS (Serrano M., et al., *Science* 267, 249–252 (1995)), consistent with the model that p16$^{Ink4a}$ operates upstream of the Rb-regulated G1/S transition (Serrano M., et al., *Science* 267, 249–252 (1995); Medema R H., et al., *Proc. Natl. Acad. Sci. USA* 92, 6289–6293 (1995); Lukas J., et al., *Nature* 375, 503–506 (1995)). Similar to its human counterpart, mouse p16$^{Ink4a}$ induced a 1.7- to 3-fold reduction in foci number when added to c-myc/RAS transfections in comparison to empty vector control (FIG. 1; A and B, p16), but failed to cause a statistically significant decrease in E1a/RAS foci formation. The addition of p19$^{ARF}$ to the cotransfections resulted in a significant reduction in foci formation by both c-myc/RAS (5–10-fold) and E1a/RAS (4- to 5-fold) (FIG. 1; A and B, p19$^{ARF}$) Moreover, E1a/RAS inhibition by p19$^{ARF}$ was not further augmented by the addition of p16$^{Ink4a}$, again consistent with the lack of effect of p16$^{Ink4a}$ in cells in which Rb has been functionally inactivated (FIG. 1C) (Serrano M., et al., *Science* 267, 249–252 (1995); Medema R H., et al., *Proc. Natl. Acad. Sci. USA* 92, 6289–6293 (1995); Lukas J., et al., *Nature* 375, 503–506 (1995)). Finally, a near complete inhibition of the transforming activity of c-myc/RAS by co-addition of p16$^{Ink4a}$ and p19$^{ARF}$ suggests functional cooperation between proteins with different mechanisms of action (see below). The anti-oncogenic profile of p19$^{ARF}$ in this assay is reminiscent of that of other cell cycle regulations, such as p53 or p21$^{CIP1}$, that function independent of or downstream to RB (for example see FIG. 1B, p21$^{CIP1}$).

Functional p53 is required for full oncogenic suppression by p19$^{ARF}$. p19$^{ARF}$ transcript levels are observed to be up-regulated in cell lines in which p53 is mutationally inactivated, MDM2 is overexpressed, or temperature-sensitive TAg is induced (Quelle D E., et al., *Cell* 83, 993–1000 (1995); Stone S., et al., *Cancer Res.* 55, 2988–2994 (1995); Mao L., et al., *Cancer Res.* 55, 2995–2997 (1995). These observations, coupled with the fact that p19$^{ARF}$, like p53, is purported to act in G1 and G2M (Quelle D E., et al., *Cell* 83, 993–1000 (1995); Quelle D E., et al., *Proc. Natl. Acad. Sci. USA* 94, 669–673 (1997), raised the possibility of a functional connection between p19$^{ARF}$ and the p53 pathway. To examine this possible relationship directly, the anti-oncogenic activity of p19$^{ARF}$ was assayed in cells rendered functionally (TAg or dominant-negative p53) or genetically (p53–/–) deficient for p53.

Figure 2A:
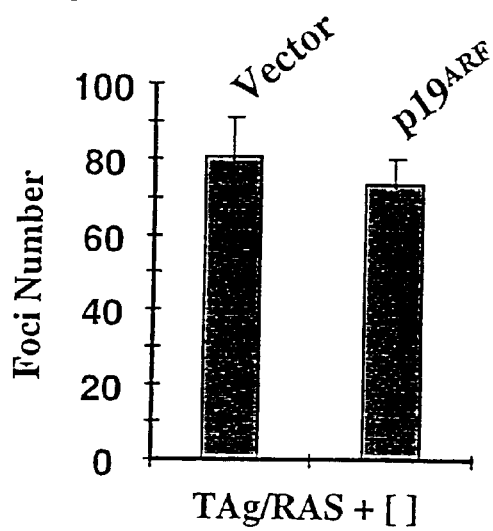
FIGS. 2A–2C.
Figure 2B:
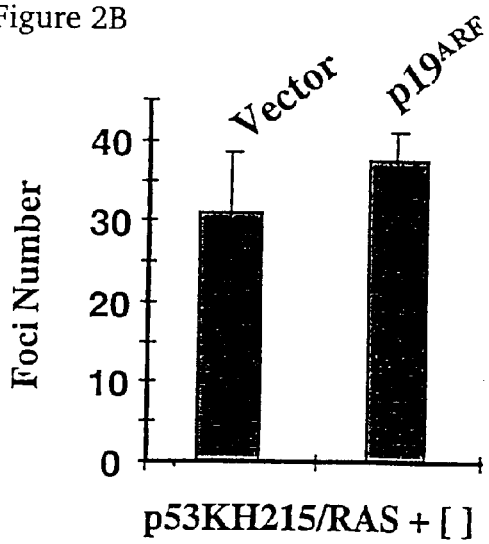
Figure 2C:
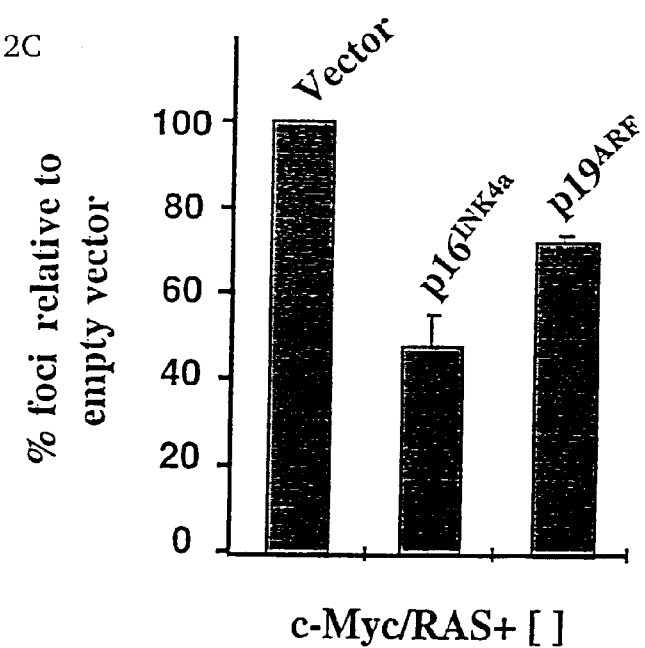

In the REF assay, the addition of p19$^{ARF}$ to TAg/RAS contransfections was found to have no effect on the number of foci generated (FIG. 2A) or on the morphological/growth characteristics of these foci (data not shown). These results suggested that p19$^{ARF}$ may require p53 for anti-oncogenic activity and ruled out the possibility that p19$^{ARF}$ acts in a nonspecific cytotoxic manner to reduce foci formation in the Myc/RAS and E1a/RAS experiments described above. Since TAg is known to engage many key pathways beyond p53 (Fanning E., *Journal of Virology* 66, 1289–1293 (1992); Van Dyke TA., *Sem. Cancer Biol.* 5, 47–60 (1994), the possible functional dependency of p19$^{ARF}$ on p53 was tested on two additional levels. First, p19$^{ARF}$ exhibited no inhibition of foci generated by cotransfection of a dominant-negative mutant form of p53, p53 KH215, and RAS in the REF assay (FIG. 2B) Second and more directly, p19$^{ARF}$-induced suppression of Myc/RAS foci formation was greatly attenuated in early passage p53–/– mouse embryonic fibroblasts (MEFs) (FIG. 2C, reduction of only 25% relative to empty vector compared to 80 to 95% in p53-competent REF cultures; see legend to FIG. 2) In contrast, p16INK4a remained fully active in this setting (FIG. 2C). Stated differently, a greater than 3-fold increase in p19$^{ARF}$ suppression is observed in the presence of p53 (compare FIG. 2C p19$^{ARF}$ with FIG. 1A p19$^{ARF}$). As such, full oncogenic suppression by p19$^{ARF}$ requires p53, but p19$^{ARF}$ may also engage p53-independent mechanisms as evidenced by the modest degree of p19$^{ARF}$ suppression (25%) that persists in the absence of p53 (p53–/–MEFs).

P19$^{ARF}$ interacts with MDM2. Results of the above focus assays prompted us to assess possible physical interactions between p19$^{ARF}$ and p53 or the MDM2 oncoprotein, a key modulator of p53 activity. Initial studies designed to examine these interactions in vitro proved inconclusive due to the propensity of p19$^{ARF}$ to interact nonspecifically with many different GST fusion proteins, this property that likely relates to the unusual amino acid composition of p19$^{ARF}$ (22% arginine (Quelle D E., et al., *Cell* 83, 993–1000 (1995)). Accordingly, low stringency co-immunoprecipitation was used to determine the nature of p19$^{ARF}$ complexes in mammalian cells. Following transfection of MDM2 and FLAG-tagged p19$^{ARF}$ (p19$^{FLAG}$) into 293T cells, an anti-FLAG antibody was used to immunoprecipitate p19FLAG complexes, and the immunoprecipitate was then immunoblotted and probed with an anti-MDM2 antibody. As shown in FIG. 3A, abundant MDM2 protein was present in the p19$^{FLAG}$ immunoprecipitates (lane 6). MDM2 was not detected in anti-FLAG immunoprecipitates in the absence of p19FLAG expression (lane 4).

Figure 3C:
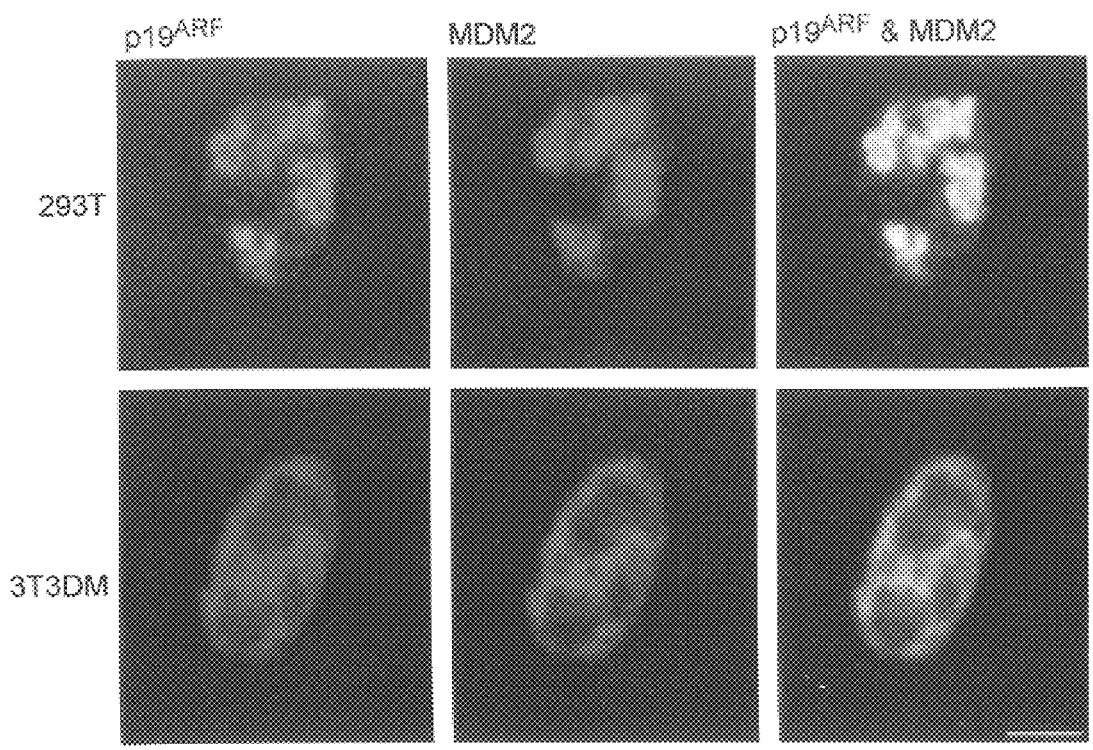
FIG. 3C shows a confocal microscopic analysis of MDM2 and p19$^{ARF}$ protein distribution in 293T and 3T3DM cells. The yellow signal indicates co-localization of the two proteins. A staining pattern similar to that observed for p19$^{Flag}$ in 293T cells has been observed previously for endogenous p19$^{ARF}$ (Quelle D E., et al., Cell 83, 993–1000 (1995)), indicating that the nucleolar localization in 293Ts is not an artifact of over-expression or epitope tagging.

Since 293T express high levels of TAG and TAG can associate with MDM2 (Brown D R., et al., *Mol. Cell. Biol.* 13, 6849–6857 (1993)), the inventors then examined the interaction between endogenous p19$^{ARF}$ and MDM2 in the absence of TAg in untransfected 3T3DM cell lines; these cells express high levels of p19$^{ARF}$ (Barak Y., et al., *Genes and Development* 8, 1739–1749 (1994)) and MDM2, the latter due to gene amplification (Cahilly-Snyder L., et al., *Som. Cell Mol. Gen.* 13, 235–244 (1987); Fakharzadeh S S., et al., *EMBO J.* 10, 1565–1569) Moreover, 3T3DM cells express several different species of MDM2 protein (p90/p85, p76/p74 and, in very low amounts, p57) arising probably through alternative processing (Barak Y., et al., *Genes and Development* 8, 1739–1749 (1994); Olson D C., et al., *Oncogene* 8, 2353–2360 (1993)). Of significance is the fact that the p76/p74 MDM2 species are missing the N-terminal p53 binding domain (Olson D C., et al., *Oncogene* 8, 2353–2360 (1993)). Employing a p19$^{ARF}$-specific antibody for immunoprecipitation, abundant MDM2 was readily detected upon Western blotting of the immunoprecipitates with anti-MDM2 antibody (lane 8), indicating that p19$^{ARF}$-MDM2 complexes exist in vivo. The p76/p74 species which lacks the p53 binding domains is also present in the immunoprecipitates indicating that p19$^{ARF}$ can interact with MDM2 independent of p53. Independent verification of the p19$^{ARF}$-MDM2 interaction was obtained through confocal microscopic analysis of the intracellular distribution of each protein. As shown in FIG. 3C, MDM2 and p19$^{ARF}$ colocalize within the nucleus: in 293T cells transfected with p19$^{FLAG}$ colocalization is seen predominantly in nucleoli and to a lesser extent in the nucleoplasm; in 3T3DM cells, both proteins are found primarily in the nucleoplasm with more modest staining in the nucleoli. Although the functional significance of the different distribution patterns in 293T and 3T3DM cells is not understood, the continued colocalization in the setting of substantial changes in intranuclear distribution further supports the concept that they complex in vivo. Finally, the same co-immunoprecipitation strategy was employed to assess whether p53 is present in p19$^{ARF}$ immunoprecipitates from untransfected 3T3DM lysates. p53 protein was readily detected, albeit at lower levels that MDM2 (not shown). In summary, these physical data serve to complement the functional link between INK4a and the p53 pathway and suggest that this link is executed on the level of MDM2.

Functional relationship of p19$^{ARF}$ to p53-related processes of apoptosis and transactivation. Two well-established systems were used to gain insight into the normal function of p19$^{ARF}$ and to determine its capacity to influence p53-dependent activities. In the first study, the inventors exploited the fact that loss of Rb function is associated with unchecked proliferation and ectopic apoptosis in lens fiber cells (Morgenbesser S D., et al., *Nature* 371, 72–74 (1994)). Significantly, this apoptotic response was shown to be dependent upon p53, because embryos doubly null for Rb and p53 showed a 4- to 5-fold reduction in apoptotic events as measured by the TUNE assay (Morgenbesser S D., et al., *Nature* 371, 72–74 (1994)). The normal function of p19$^{ARF}$ was assessed by generating embryos doubly null for Rb and INK4a to specifically evaluate p19$^{ARF}$, as opposed to p16$^{INK4a}$, function in a p53 apoptotic pathway. This line of reasoning based upon the finding that p16Ink4a, operates upstream of Rb and has no discernable growth effects in Rb null cells (Serrano M., et al., *Science* 267, 249–252 (1995); Medema R H., et al., *Proc. Natl. Acad. Sci. USA* 92, 6289–6293 (1995); Lukas J., et al., *Nature* 375, 503–506 (1995)); and see FIG. 1B above).

As shown in FIG. 4, histological analyses of many Rb–/– and Rb–/–, INK4a–/– lenses staged 13.5 or 14.5 revealed a clear increase in the number of nuclei compared with age matched wildtype lenses (compare panels B or C with A) Moreover, doubly null lenses had a 25% increase in the number of nuclei are Rb−/− lenses (compare panels C and B). While the lens fiber region of normal lenses does not exhibit proliferative activity ((Morgenbesser S D., et al., Nature 371, 72–74 (1994); panel D)), inappropriate cell cycle progression was confirmed throughout the lens fiber region of Rb−/− and Rb−/−, INK4a−/1-lenses by the large number of cells positive for 5-bromo-2'-deoxyuridine (BrdU) (panels E and F). When normalized to the total number of nuclei, the degree of BrdU incorporation in Rb−/− and doubly null lens fiber cells was very similar in age-matched lenses (p<0.001). In contrast, when lens fiber cell apoptosis was measured, the number of TUNEL-positive nuclei was significantly and consistently reduced in the doubly null lenses relative to that present in the Rb-deficient lenses (compare panels H and I; and see J for quantitation; p=0.003). The level of reduction achieved with loss of $p19^{ARF}$ function was less than that reported previously with loss of p53 ((Morgenbesser S D., et al., Nature 371, 72–74 (1994)); reduction of 50 to 60% for Rb−/−, INK4a−/− versus 75 to 85% for Rb−/−, p53−/−) These studies show that the efficient execution of an apoptotic response known to be dependent upon p53 requires INK4a gene function, a function that is most likely served by $p19^{ARF}$.

These findings, together with the cell transformation studies and MDM2 interaction, are consistent with the view that $p19^{ARF}$ may function normally to suppress neoplasia via enhancing p53's ability to eliminate inappropriately cycling cells. Since many biological activities of p53 are highly dependent upon its capacity to function as a sequence-specific transcription factor, we tested whether $p19^{ARF}$ positively regulates p53 transactivation potential. 293T cells were transfected with a fixed amount of a p53 expression construct and CAT reporter bearing multimerized p53 binding sites (PG13CAT) and an increasing amount of a $p19^{ARF}$ expression construct. A progressive increase in the level of CAT activity was observed upon the addition of $p19^{ARF}$ in a dose-dependent manner (FIG. 4C). Moreover, the addition of $p19^{ARF}$ to Myc reporter assays did not affect Myc transactivation potential (data not shown). The ability of $p19^{ARF}$ to enhance p53 transactivation potential and the importance of this property of p53 in p53-mediated tumor suppression provides a possible basis for the anti-oncogenic actions of $p19^{ARF}$.

Distinct and cooperative effects of $p16^{INK4a}$ and $p19^{ARF}$ in the suppression of primary cell transformation. The anti-oncogenic potencies of the two ink4a gene products were tested in the rat embryo fibroblast (REF) cotransformation assay (Land et al., 1983, Nature 304, 596–602) against various oncogene combinations (e.g., Myc/RAS, E1a/RAS or SV40 Large T Antigen (T-Ag)/RAS). This approach has been used extensively to provide a quantitative measure of anti-oncogenic activity and allow for placement of these activities along known growth control pathways (Lahoz et al., 1997, PNAS USA June 7. 91, 5503–5507; Schreiber-Agus et al., 1995, Cell 80, 777–786; Alland et al., 1997, Nature 1997. May 1. 387, 49–55). In the first series of experiments, the degree of inhibition of E1a/RAS-versus Myc/RAS-induced foci formation by $p19^{ARF}$, $p16^{Ink4a}$, or both was investigated. As shown in FIG. 6, addition of mouse $p16^{Ink4a}$ induced a 1.7- to 3-fold reduction in foci number when added to c-myc/RAS transfections (panel A, p16INK4a) and failed to cause a statistically significant decrease in E1a/RAS foci counts (panel B, p16INK4a); these results are identical to our previous report for the human $p16^{Ink4a}$ (Serrano et al., 1995, Science 267, 249–252). Since E1A inactivates the Rb protein, the failure of $p19^{INK4a}$ to suppress EL/RAS transformation is as expected (Serrano et al., 1995, Science 267, 249–252; Medema et al., 1995, Proc. Natl. Acad. Sci. USA 92, 6289–6293; Lukas et al., 1995, Nature 375, 503–506). In the same cotransfection experiments, addition of $p19^{ARF}$ resulted in marked foci reductions in c-myc/RAS (5- to 10-fold) as well as E1a/RAS (4- to 5-fold) cotransfections (panels A and B, $p19^{ARF}$). E1a/RAS inhibition by $p19^{ARF}$ was not further augmented by the addition of $p16^{Ink4a}$ (panel B, compare $p19^{ARF}$ and $p16^{Ink4a}+p19^{ARF}$). In contrast, co-addition of $p16^{Ink4a}$ and $p19^{ARF}$ resulted in a complete inhibition of c-myc/RAS transformation. Thus, the distinct activity profiles of $p16^{INK4a}$ and $p19^{ARF}$ (i.e., E1a/Ras transfections), together with their additive effects in the c-myc/RAS transfections, suggest that these proteins suppress neoplasia through separable but cooperative mechanisms of action (see below).

Figure 6D:
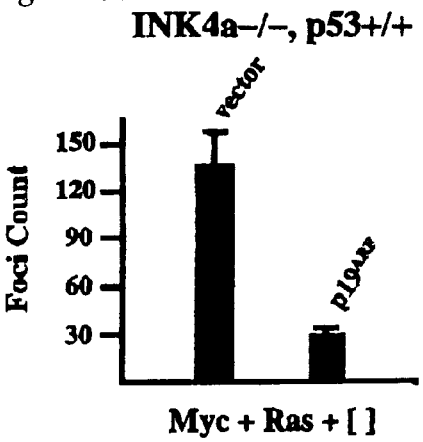
Figure 6D:
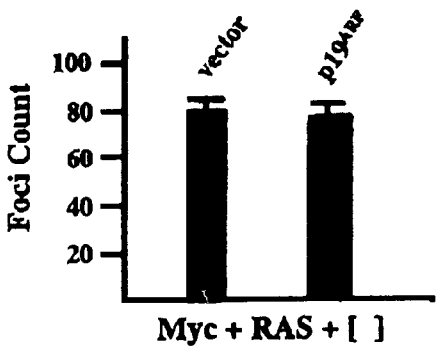

Functional p53 is required for full oncogenic suppression by $p19^{ARF}$. The cell cycle inhibitory effects of $p19^{ARF}$ in primary MEF cultures have been shown to be p53-dependent (Kamijo et al., 1997a, Cell 91, 649–659). To examine the possibility that $p19^{ARF}$ may also act in a p53-dependent manner to suppress cellular transformation, the inventors employed cells rendered functionally (T-Ag or dominant-negative p53) or genetically (p53−/−) deficient for p53 in transformation assays. The addition of $p19^{ARF}$ to TAg/RAS cotransfections was found to have no effect on the number of foci generated in the REF assay (FIG. 6C) or on the morphological/growth characteristics of these foci (data not shown). Since T-Ag is known to engage many pathways beyond p53 (Fanning, 1992, Journal of Virology 66, 1289–1293; Van Dyke, 1994, Sem. Cancer Biol. 5, 47–60), the ability of $p19^{ARF}$ to suppress transformation in two other contexts was then assessed. First, in comparison to the addition of an empty vector control, the addition of $p19^{ARF}$ did not affect the number of foci generated cotransfection of a dominant-negative mutant form of p53 (p53 KH215) and RAS in the REF assay (FIG. 6C) Second, potent $p19^{ARF}$-induced suppression of Myc/RAS foci formation was observed in early passage Ink4a−/− mouse embryonic fibroblasts (MEFs), but this suppression was completely eliminated in MEFs doubly null for Ink4a and p53 (FIG. 6D). These results strongly suggest that $p19^{ARF}$ does not act in a nonspecific cytotoxic manner to reduce foci formation in the Myc/RAS and E1a/RAS experiments described above. Instead, these results appear to assign specificity to the anti-oncogenic actions of $p19^{ARF}$. More specifically, in accord with the recently reported cell cycle studies (Kamijo et al., 1997a, Cell 91, 649–659), these findings support the hypothesis that $p19^{ARF}$ acts in a p53-dependent manner to inhibit cellular transformation.

$p19^{ARF}$ associates with MDM2 in vivo. To gain insight into the mechanistic basis for the functional link between $p19^{ARF}$ and the p53 pathway, co-immunoprecipitation experiments were performed to assess potential physical interactions between $p19^{ARF}$ and p53 or the p53-associated protein, MDM2. Since endogenous levels of these proteins are very low in normal primary cells (Levine, 1997, Cell 88, 323–331), the composition of the $p19^{ARF}$ complexes was determined following co-transfection of various expression constructs (including one encoding a FLAG epitope-tagged $p19^{ARF}$ protein, $p19^{FLAG}$) or through the use of different tumor cell lines expressing some or all of these proteins. As shown in FIG. 7A, IP-Western blot assays readily detected p19$^{FLAG}$ in anti-p53 immunoprecipitates following co-transfection with p53, MDM2 and p19$^{FLAG}$ (lane 2) but not with p53 and p19$^{FLAG}$ (lanes 3 and 4). The requirement of MDM2 overexpression to reveal a p$_{53}$–p19$^{FLAG}$ interaction was also observed following either anti-p53 or anti-FLAG immunoprecipitations of metabolically labeled transfected cells (data not shown). These results demonstrate that p53, MDM2 and p19$^{FLAG}$ can exist as components of a multi-protein complex in vivo. Moreover, the requirement for abundant MDM2 to detect p53–p19$^{FLAG}$ interaction suggested that MDM2 serves as a bridging molecule, or that MDM2 induces changes in steady-state levels of p19$^{FLAG}$, among other possibilities. The possibility that MDM2 overexpression stabilizes the level of p19$^{FLAG}$ was ruled out by Western blot analysis showing equivalent levels of p19$^{FLAG}$ in 293T cells following transfection of MDM2 and p19$^{FLAG}$ or of p19$^{FLAG}$ alone (data not shown). Moreover, although MDM2 can target p53 for degradation in some cell types (Haupt et al., 1997, Nature 387, 296–299; Kubbutat et al., 1997, Nature 387, 299–303), the levels of endogenous p53 in 293T cells remain constant following co-transfection and over-expression of MDM2 (data not shown) due to the presence of T-Ag (Henning, et al., 1997, Journal of Virology 71, 7609–7618).

To examine more directly whether p19$^{FLAG}$ can associate with MDM2, co-immunoprecipitation studies were conducted in metabolically labeled 293T cells and in 3T3DM (amplified for MDM2) and SAOS2 cells (null for p53). In the 293T cells (FIG. 7B and C), MDM2 was readily detected in anti-FLAG immunoprecipitates following co-transfection with p19$^{FLAG}$ and MDM2 (lane 8) and but not with either empty vector (lane 6), p19$^{FLAG}$ alone (lane 5) or MDM2 alone (lane 7). Correspondingly, anti-MDM2 immunoprecipitations confirmed the MDM2-p19$^{FLAG}$ association in the p19$^{FLAG}$ and MDM2 cotransfections (lane 12). In addition, the endogenous p19$^{ARF}$ band was present in the anti-MDM2 immunoprecipitates (lane 9) and the signal intensity of this band diminished upon co-transfection of p19$^{FLAG}$ (lane 12), this likely due to competition for a common binding site in the MDM2 complex. In each of these experiments, Western blot analyses of lysates that were run in parallel confirmed the identity of p19$^{FLAG}$ and MDM2 bands (data not shown). The interaction between p19$^{FLAG}$ and MDM2 in 293T cells was also demonstrated by co-immunoprecipitation in both low and high stringency conditions yielding identical results (FIG. 7C, lanes 18 and 19, respectively).

To address whether the interaction of T-Ag with MDM2 and p53 (Brown et al., 1993, Mol. Cell. Biol. 13, 6849–6857) alters the composition of MDM2/p53/p19$^{ARF}$ complexes in T-Ag expressing 293T cells, the interaction between endogenous p19$^{ARF}$ and MDM2 was examined in 3T3DM cell lines. These cells do not express T-Ag but do express high levels of p19$^{ARF}$ (Quelle et al., 1995b, Cell 83, 993–1000) and MDM2, the latter due to gene amplification (Cahilly-Snyder et al., 1987, Som. Cell Mol. Gen. 13, 235–244; Fakharzadeh et al., 1997, EMBO J. 10, 1565–1569). Of note, 3T3DM cells express several alternatively processed species of MDM2 protein (FIG. 7D, lane 20–21, p90/p85, p76/p74 and, in very low amounts, p57) (Barak, et al., 1994, Genes and Development 8, 1739–1749; Olson et al., 1993, Oncogene 8, 2353–2360). Employing a p19$^{ARF}$-specific antibody for immunoprecipitation, abundant MDM2 was readily detected upon Western blotting of the immunoprecipitates with anti-MDM2 antibody (lane 21), further substantiating that p19$^{ARF}$ and MDM2 interact in vivo. Moreover, the p76/p74 species which lacks the N-terminal p53 binding domain (Olson et al., 1993, Oncogene 8, 2353–2360) is also present in the immunoprecipitates (lane 21, asterisk marks the p76/p74 forms of MDM2 that do not interact with p53), suggesting that p19$^{ARF}$ can interact with MDM2 independent of MDM2's interaction with p53. To confirm this point, anti-FLAG immunoprecipitation following co-transfection of p19$^{FLAG}$ and MDM2 into p53 null SAOS2 cells yielded abundant MDM2 signal (FIG. 7E, lane 26). Finally, confocal microscopic analysis of the intracellular distribution of each protein demonstrated identical subnuclear localization patterns for p19$^{ARF}$ and MDM2 in both 293T and 3T3DM cells (FIG. 7F, 293T cells shown).

Next, a series of plasmids encoding full-length MDM2 or various mutant derivatives was tested for the ability to associate with FLAG-tagged p19$^{ARF}$ by coimmunoprecipitation/Western blotting analyses in 293T and SAOS2 cells. The results of these studies, as shown in FIG. 8, point to a complex interaction profile in which p19$^{FLAG}$ engages multiple sites within MDM2. Specifically, the p19$^{FLAG}$-MDM2 interaction was preserved with deletion of the entire carboxy terminal half of MDM2 (221–491, lanes 12–13) but this interaction was abolished with a slightly larger deletion (155–491, compare lysate in lane 10 to immunoprecipitation in lane 11). While these observations demonstrate an essential role for MDM2 amino acid residues 154–221 in p19$^{ARF}$ binding, an internal deletion mutant of these residues was still capable of p19$^{ARF}$ association in the two cell types (155–221, lanes 6–7 293T, lanes 8–9 SAOS2) The persistent binding of the 155–221 mutant may reflect additional points of contact in the carboxy terminus of MDM2 that cooperate in p19$^{ARF}$ binding. This view is supported by the diminished interaction between p19$^{FLAG}$ and the 221–491 mutant in SAOS2 cells (compare lanes 12, 13 to 14, 15) and also suggests the participation of bridging molecules in 293T that facilitate the p19$^{FLAG}$-MDM2 interaction (e.g., p53, T-Ag, etc.). Taken together, the carboxy-terminal localization, coupled with the ability of a p53-binding deficient mutant of MDM2 to remain competent for p19$^{ARF}$ binding (lane 1), suggest that p19$^{ARF}$'s effects upon known properties of MDM2 or p53 (see below) likely do not result from a disruption of the physical association between MDM2/p53 by p19$^{ARF}$. Further support that p19$^{ARF}$ and p53 interact with non-overlapping regions of MDM2 comes from the observations that p19$^{ARF}$ and p53 can co-exist in MDM2 complexes and that p53 immunoprecipitations followed by Western analysis for MDM2 showed similar levels of MDM2 relative to lysate in the presence or absence of p19$^{ARF}$ (data not shown).

Functional relationship of p19$^{ARF}$ to MDM2 and p53. The physical association between p19$^{ARF}$ and MDM2 establishes a clear connection between a product of the INK4a gene and the p53 pathway. To understand the functional implications of the p19$^{ARF}$-MDM2 interaction, the capacity of p19$^{ARF}$ to (1) inhibit MDM2 cotransformation activity, (2) block MDM2-induced degradation of p53, and (3) enhance p53-related activities such as transcription and apoptosis was assessed.

Figure 9A:
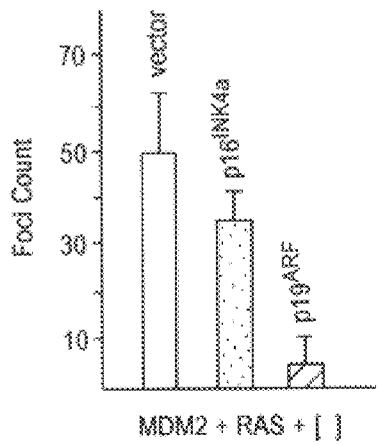
FIGS. 9A–9D.
Figure 9C:
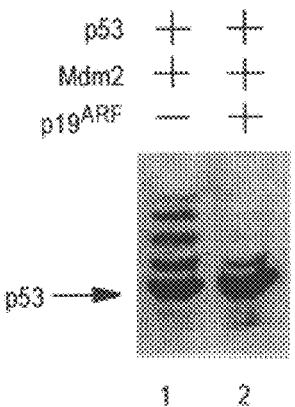
Figure 9B:
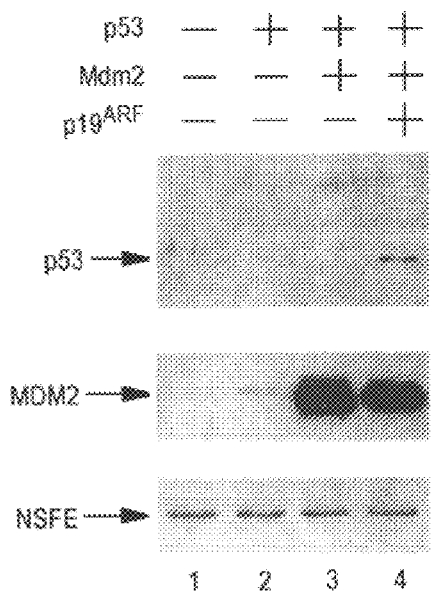
Figure 9D:
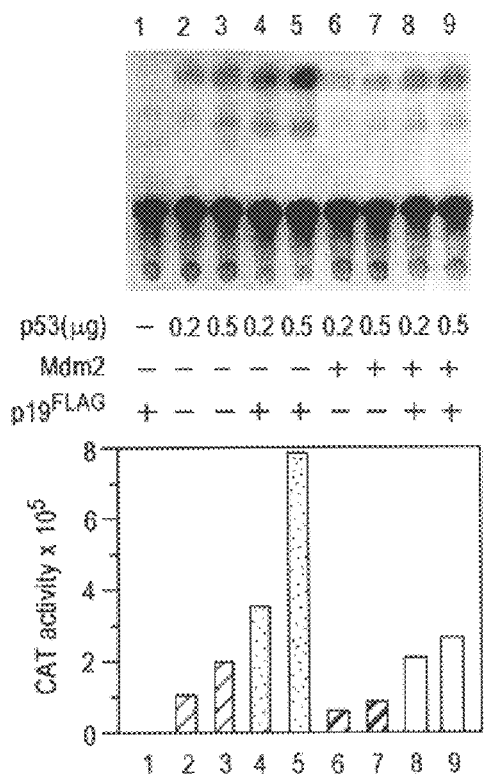

Transformation Studies. For the MDM2 transformation studies, the inventors took advantage of the capacity of MDM2 to cooperate with activated RAS to effect the malignant transformation of early passage REFs (Finlay, 1993, Molecular & Cellular Biology 13, 301–306) In four independent experiments, the inventors observed that the addition of p19$^{ARF}$ to MDM2/RAS cotransfections resulted in a dramatic reduction in foci numbers, e.g., 40 foci versus 3 foci (FIG. 9A). Moreover, compared with MDM2/RAS and vector controls, the MDM2/RAS transformed foci emerging in the p19$^{ARF}$ cotransfections exhibited a less transformed morphology (data not shown).

p53 protein stability studies. Next, we examined the consequences of p19$^{ARF}$ over-expression on a key biochemical property of MDM2, namely MDM2's ability to promote the rapid degradation of p53 (Haupt et al., 1997, Nature 387, 296–299; Kubbutat et al., 1997, Nature 387, 299–303). For this study, HeLa cells were transiently transfected with the various expression constructs listed in FIG. 9B and the levels of p53 were examined by Western blot analysis. As reported previously (Haupt et al., 1997, Nature 387, 296–299), p53 steady-state levels were markedly reduced in cells co-transfected with p53 and MDM2 as opposed to p53 alone (FIG. 9B, top panel, compare lanes 2 and 3). When p19$^{ARF}$ was added to the p53+MDM2 co-transfections, a striking restoration in p53 levels was observed (lane 4). Equal loading of protein was confirmed by reprobing the blots with an anti-FLAG antibody, which detects a non-specific background band (NSFE) (FIG. 9B, bottom panel) as well as by Ponceau Red staining of blots (data not shown). The precise mechanism through which p19$^{ARF}$ operates to interfere with MDM2-induced degradation is not known. Nevertheless, it is interesting that MDM2 induces a ladder of more slowly migrating bands of p53 (FIG. 9C, lane 1), thought to represent ubiquitinated forms of p53 bound for proteasomal degradation (Haupt et al., 1997, Nature 387, 296–299; Kubbutat et al., 1997, Nature 387, 299–303) This ladder is significantly reduced in the presence of abundant p19$^{ARF}$ (FIG. 9C, lane 2), suggesting that p19$^{ARF}$ inhibits polyubiquitination of p53 triggered by MDM2. Loss of this MDM2-induced ladder was also observed after transfection of p19$^{ARF}$, p53 and MDM2 into two other cell lines, H1299 and SAOS2 (data not shown). Although our studies strongly suggest that p19$^{ARF}$ blocks MDM2-induced degradation of p53, they do not exclude other possibilities such as p19$^{ARF}$ stabilizing p53 in an MDM2-independent manner.

Regulation of p53 transactivation activity. Enforced expression of p19$^{ARF}$ in primary mouse cells results in the induction of p21$^{CIP1}$ (a p53-responsive gene (El-Deiry et al., 1993, Cell 75, 817–825)), but only if these cells that possess functional p53 (Kamijo et al., 1997a, Cell 91, 649–659) (and JP and RD, unpublished observations) These results suggest that p19$^{ARF}$ can enhance the transactivation activity of p53 (Kamijo et al., 1997a, Cell 91, 649–659), perhaps through its ability to counteract MDM2. To test this directly, SAOS2 cells were transfected with a CAT reporter bearing multimerized p53 binding sites in its promoter and with a combination of expression constructs listed in FIG. 9D. Since these cells are null for p53, CAT activity was detected only in the presence of transfected p53 (compare lane 1 with lanes 2 and 3). Transfection of p19$^{ARF}$ resulted in a further increase in reporter gene activity (lanes 4 and 5), an increase that takes place in the presence of detectable endogenous MDM2 levels resulting from exogenous p53 expression (data not shown). As reported previously (Brown et al., 1993, Mol. Cell. Biol. 13, 6849–6857; Momand et al., 1992, Cell 69, 1237–1245), addition of MDM2 to the p53 cotransfections led to a decrease in reporter activity (compare lanes 6 and 7 with lanes 2 and 3) and this effect was abolished with the addition of p19$^{ARF}$ (lanes 8 and 9).

In light of the data presented above, enhanced p53 transactivation could result from increased p53 levels due to p19$^{ARF}$-induced stabilization of p53. However, the findings that over-expression of p19$^{ARF}$ leads to stabilized p53 complexes which also contain MDM2 (FIG. 7) and that MDM2 binds to and masks the p53 transactivation domain raises questions as to how p53 transactivation can be restored by p19$^{ARF}$ in the setting of high levels of MDM2. Among several possibilities are that a subset of transactivation domains in the stabilized p53 tetramer are not bound by MDM2, that p19$^{ARF}$ may function to block MDM2-induced repression of basal transcription, or that p19$^{ARF}$ activates p53 transactivation in an MDM2-independent manner. The resolution of this point will require further analysis in vitro. In summary, these results demonstrate that p19$^{ARF}$ can enhance a key function of p53, its capacity to function as a sequence-specific transcription factor.

INK4a-deficiency attenuates apoptosis in vivo. The observed effects of p19$^{ARF}$ on p53 dependent transactivation (this study) and gene expression (Kamijo et al., 1997, Cell 91, 649–659), and the established importance of p53 in apoptosis prompted us to assess whether loss of p19$^{ARF}$ may affect the degree of apoptosis in vivo. The inventors have shown previously that the developing mouse lens represents an ideal system for such an analysis since loss of Rb function therein is associated with unchecked proliferation and apoptosis in lens fiber cells and this apoptotic response is highly dependent upon p53 (Morgenbesser et al., 1994, Nature 371, 72–74) As an indirect assessment of p19$^{ARF}$ effects upon this phenotype, rates of proliferation and apoptosis were compared in embryos singly null for Rb or doubly null for Rb and INK4a. Since p16$^{INK4a}$ is believed to be without effect when Rb is absent, the doubly null lenses were taken to be the functional equivalent of Rb−/−, p19$^{ARF}$−/− lenses.

Figure 10A:
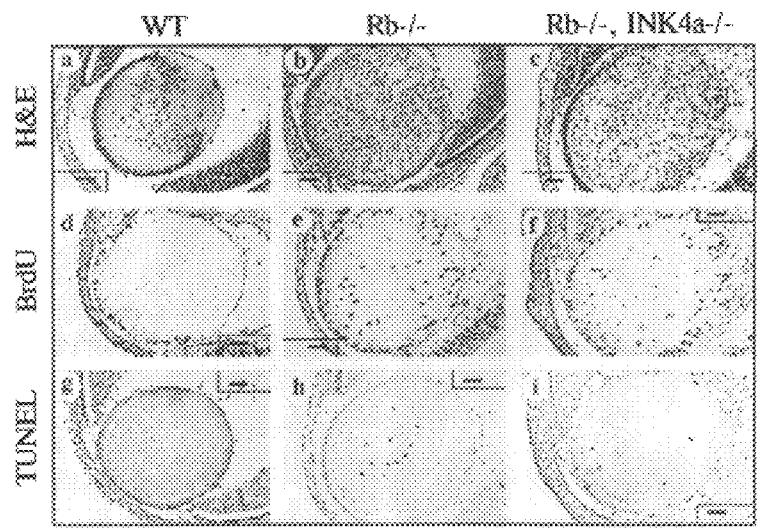
FIGS. 10A and 10B.
Figure 10B:
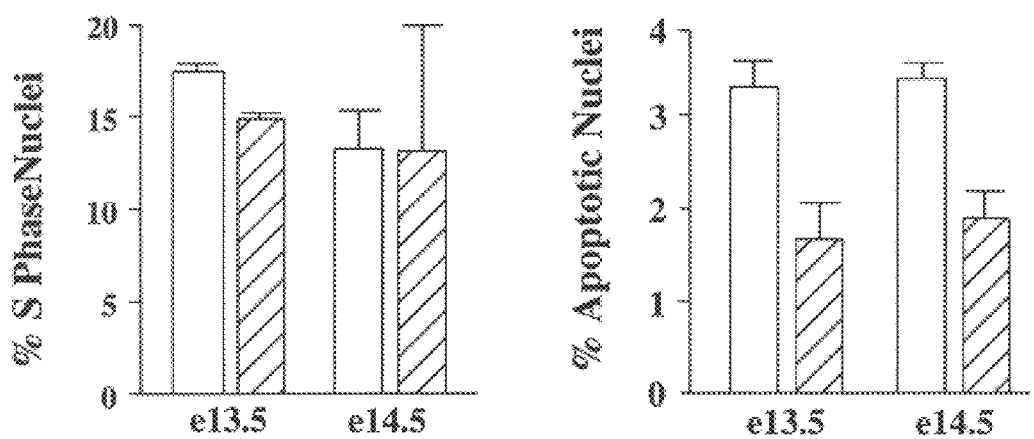

Histological analyses of more than 15 Rb−/− and Rb−/−, ink4a−/− lenses revealed a clear increase in the number of nuclei compared with age-matched wildtype lenses (FIG. 10A, compare panels b and c with a). Moreover, doubly null lenses had a 25% increase in the number of nuclei over Rb−/− only lenses. While the lens fiber region of normal or ink4a−/− lenses does not exhibit proliferative activity (Morgenbesser et al., 1994, Nature 371, 7274) (FIG. 10A, panel d, ink4a−/− not shown), inappropriate cell cycle progression was confirmed throughout the lens fiber region of Rb−/− and Rb−/−, ink4a−/− lenses by the large number of cells staining positive for 5-bromo-2′-deoxyuridine (BrdU) incorporation (FIG. 10A, panels e and f) When normalized to the total number of nuclei, the degree of BrdU incorporation in Rb−/− and doubly null lens fiber cells was very similar in age-matched lenses (FIG. 10B left panel p<0.001). In contrast, when lens fiber cell apoptosis was measured, the number of TUNEL-positive nuclei was significantly and consistently reduced in the doubly null lenses relative to that present in the Rb-deficient lenses (FIG. 10A, compare panels h and i; FIG. 10B right panel) These studies show that the efficient execution of an apoptotic response known to be dependent upon p53 requires full ink4a gene function. The dual elimination of both ink4a gene products precludes a definitive assignment to p19$^{ARF}$ since it remains theoretically possible that p16$^{INK4a}$ may play a role in the apoptotic process through an Rb-independent pathway. However, these findings may explain how p19$^{ARF}$ functions as a suppressor of neoplasia, namely through its capacity to enhance the p53-mediated elimination of inappropriately cycling cells in vivo.

III. Discussion

Analysis of tumor associated mutations affecting the INK4a locus in mouse (data not shown) and humans (Kamb A., et al., *Science* 264, 436–440 (1994)) has revealed a high incidence of homozygous co-deletion of p16$^{Ink4a}$ and p19$^{ARF}$ sequences. These observations, together with the functional and physical evidence presented here, lead us to propose that p19$^{ARF}$ contributes to the anti-oncogenic activity of INK4a and that the frequent elimination of both INK4a gene products reflects a requirement to disable two functionally distinct growth inhibitory pathways. From a mechanistic standpoint, full oncogenic suppression by p19$^{ARF}$ requires p53 as evidence by a significant reduction in p19$^{ARF}$ activity in the presence of SV40 TAg or a dominant negative mutant of p53 or in the absence of p53 (p53−/− MEFs). The ability of p19$^{ARF}$ to enhance p53-related functions in the Rb-deficient lens (apoptosis) and in reporter assays (transactivation) suggests that p19$^{ARF}$ acts as an activator of p53 activity. Based upon the existence of a p19$^{ARF}$-MDM2 interaction in cells, it is tempting to speculate that p19$^{ARF}$ could function to neutralize MDM2-induced inhibition of p53. However, it is important to point out that p19$^{ARF}$ also associates with the form of MDM2 (p76/p74) which lacks the N-terminal p53 interaction pocket, suggesting mechanisms other than a competitive occupation of the p53 interaction pocket by p19$^{ARF}$. Moreover, since other MDM2 species that interact with p19$^{ARF}$ can also interact with p53, there may be additional interactions between p19$^{ARF}$ and p53 in the absence of MDM2. While a detailed accounting of these interactions should provide important mechanistic clues, the findings of this report are the first to establish a clear connection between the ink4a gene and the p53 tumor suppressor pathway.

One-gene-two-products-two-pathways: Implications for tumorigenesis. The potential to disrupt two essential growth control pathways through a single genetic hit may provide an explanation for: (i) the exceedingly high rate of Ink4a gene deletion in may human tumors and their derivative cell lines (Kamb A., et al., *Science* 264, 436–440 (1994)); (ii) the high incidence of spontaneous tumors in mice lacking Ink4a exon 2/3 sequences (Serrano, M., et al., *Cell* 85, 27–37 (1996)); and (iii) the strong connection between tumorigenesis and the Ink4a gene as opposed to other genes encoding cyclin-dependent kinase inhibitors, such as INK4b, p21$^{CIP1}$ and p27$^{KIP120}$. Specifically, mice lacking INK4b exhibit a very low incidence of spontaneous tumor formation (E. Latres, C. Cordon-Cardo and M. Barbacid, unpublished), p21$^{CIP1}$-deficient mice remain tumor free (Elledge S J., et al., *TICB* 6, 388–392 (1996)), and although p27$^{KIP2}$-deficient mice can develop intermediate lobe pituitary hyperplasia or adenoma, these neoplasma rarely progress to malignant pituitary tumors (Elledge S J., et al., *TICB* 6, 388–392 (1996)). Similarly, in human cancers, the frequent alteration of ink4a contrasts sharply with an overall lower rate of ink4b mutation/deletion (Cordon-Cardo C., *Am. J. Pathol.* 147, 545–560 (1995)) and infrequent mutations in p21$^{CIP1}$ and p27$^{KIP120}$. Such biological correlates would not have been anticipated in view of the highly similar biochemical and growth suppressive activities of these cyclin-dependent kinase inhibitors. What makes the INK4a gene so unique? Based upon the findings of this study, we propose that INK4a's potent tumor suppressor activity results from its ability to encode two different anti-oncogenic proteins with cooperating modes of action. One prediction of this hypothesis is that tumors deficient for both p16$^{Ink4a}$ and p19$^{ARF}$ would be less likely to harbor Rb or p53 mutations. Furthermore, p19$^{ARF}$-sparing ink4a mutations could be associated with alterations involving other components of the p53 pathway (e.g., MDM2 amplification or loss of p53 function). It is important to emphasize that elimination of p19$^{ARF}$ would not preclude p53 mutation since p53 plays multiple roles in suppressing neoplastic growth that are likely to extend beyond the p19$^{ARF}$-p53 connection. Stated differently, loss of function mutations of p19$^{ARF}$ would be predicted to decrease the frequency of, but not eliminate, tumor-associated p53 mutations.

In light of the above observation, the inventors reexamined reported Ink4a and p53 mutations in the same human cancers (Gruis N A., et al., *Am. J. Pathol.* 146, 1199–1206 (1995); Hangaishi A., et al., *Blood* 87, 4949–4958 (1996); Heinzel P A., et al., *Intl. J. Cancer* 68, 420–423 (1996); Kinoshita I., et al., *Cancer Res.* 56, 5557–5562 (1996); Newcomb E W., et al., *Mol. Carcin* 14, 141–146 (1995); Brenner A., et al., *Clin. Cancer Res.* 2, 1993–1998 (1996)). These tumor types included melanoma, carcinomas (bladder, oral, and lung carcinomas), and various lymphoid neoplasms (B-cell chronic lymphocytic leukemia, Hodgkin and Non-Hodgkin lymphomas). Our analysis demonstrated a reciprocal relationship between these two genes, since Ink4a-deficient (p16$^{Ink4a}$+p19$^{ARF}$) cancers rarely exhibit p53 mutant products (Gruis N A., et al., *Am. J. Pathol.* 146, 1199–1206 (1995); Hangaishi A., et al., *Blood* 87, 4949–4958 (1996); Heinzel P A., et al., *Intl. J. Cancer* 68, 420–423 (1996); Kinoshita I., et al., *Cancer Res.* 56, 5557–5562 (1996); Newcomb E W., et al., *Mol. Carcin* 14, 141–146 (1995); Brenner A., et al., *Clin. Cancer Res.* 2, 1993–1998 (1996)). In 518 tumors analyzed, the mutation rates were 18% for p16$^{INK4a}$, 14% for p53, and 4% for both. Ink4a point mutations that result in single amino acid changes in the p16$^{INK4a}$ ORF were reanalyzed to determine the genetic status of the p19$^{ARF}$ ORF. Only 9 (<2%) of 405 evaluable cases harbored p53 and p19$^{ARF}$ mutations. Since all 9 cases also had alterations in p16$^{INK4a}$ it remains possible that p19$^{ARF}$ mutations was incidental to that of p16$^{INK4a}$ in those tumors. Moreover, the impact of these p19$^{ARF}$ mutations on p19$^{ARF}$ function remains to be determined. These observations point to the need for a revisited analysis of mutations for p19$^{ARF}$, p19$^{INK4a}$, p53 and MDM2 in the same tumor samples. In fact, the most common point mutation in the p19$^{ARF}$ reading frame (a P93L substitution (Quelle et al., 1995b, Oncogene 11, 635–645)) has been shown by the inventors to be functionally indistinguishable from wild-type p19$^{ARF}$. This is evidenced by the facts that the p19$^{ARF}$ (P93L) mutant is fully active in suppressing Myc/RAS and MDM2/RAS in the REF assay and in stabilizing p53 in the presence of high MDM2 levels (data not shown). These observations point to the need for a revisited analysis of mutations for p19$^{ARF}$, p16$^{INK4a}$, p53 and MDM2 in the same tumor samples. Although available data (Kamijo et al., 1997a, Cell 91, 649–659) (and this paper) do not permit conclusion that p19$^{ARF}$ and p53 mutations are mutually exclusive, the distinctly uncommon occurrence of co-mutation of p53 and p19$^{ARF}$ supports the view that they operate through common genetic pathways for at least a significant portion of their tumor suppressor activity.

Therapeutic implications. The studies by the inventors demonstrating that dominant interference with p53 nullifies p19$^{ARF}$ suppression presage that the introduction of p19$^{ARF}$ into tumors rendered functionally or genetically deficient for p53 would fail to respond clinically. Such an outcome agrees well with the observations of Quelle et al. (Quelle D E., et al., *Cell* 83, 993–1000 (1995)), who reported high levels of p19$^{ARF}$ mRNA only in p53-null cell lines, suggesting a functional interrelationship between these two proteins. By extension, an improved therapeutic outcome in p53-null tumors would be expected with regimens that included both p53 and p19$^{ARF}$ as opposed to p53 alone. Finally, in tumors null for ink4a or for both Rb and p53, the addition of p16$^{Ink4a}$ to a p19$^{ARF}$/p53 combination may actually diminish the efficacy of p19$^{ARF}$/p53 based upon the potent growth arresting activity of p16$^{INK4a}$ and a possible diminution in elimination of tumor cells by programmed cell death. In agreement with this prediction are recent studies demonstrating that p16$^{Ink4a}$-mediated cell cycle arrest resulted in a dramatic increase in resistance to chemotherapeutic agents (Stone S., et al., *Cancer Res.* 56, 3199–3202 (1996)).

The connection to the RB and p53 pathways has important implications for understanding the prominent role served by INK4a in cellular growth, survival, senescence and neoplasia. In normal cells, the capacity of a single gene to encode regulations of both RB and p53 may enable the coordination of two pathways known to be integral to the entry of normal cells into replicative senescence. In cancer cells, the loss of two distinct tumor suppressor products with the elimination of a single gene would provide a strategic genetic route to neoplasia and, as such, may account for the frequent-involvement of INK4a in the development of a broad spectrum of malignancies.

Figure 11A:
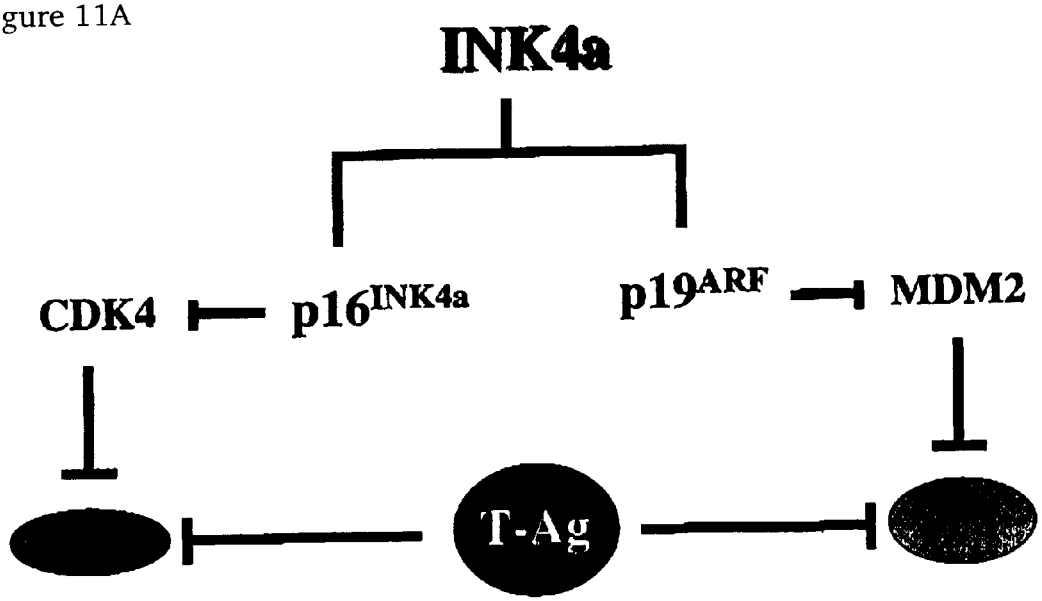
FIGS. 11A and 11B.
Figure 11B:
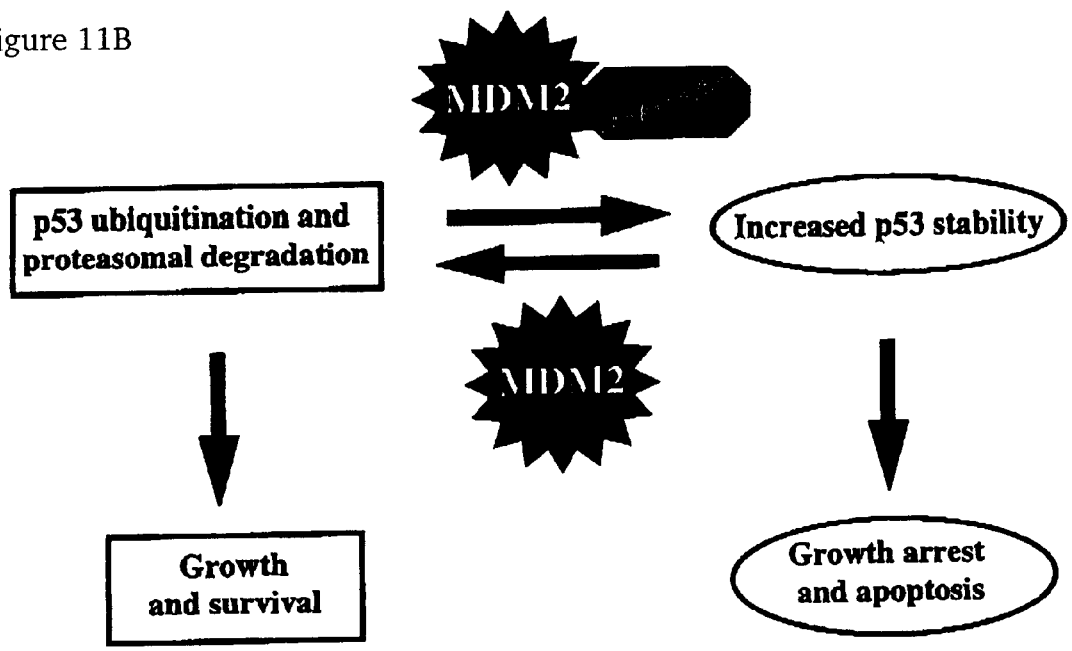

Recent studies in cell culture and with knockout mouse models have determined that the second product of the Ink4a locus, namely p19$^{ARF}$, functions as a potent growth and tumor suppressor that exerts its actions upstream of p53 (Kamijo et al., 1997a, Cell 91, 649–659; Quelle et al., 1997, Proc. Natl. Acad. Sci. USA 94, 669–673; Chin et al., 1997, Genes and Development 11, 2822–2834). Here the inventors refined this connection between p19$^{ARF}$ and the p53 pathway by demonstrating that p19$^{ARF}$ physically associates with MDM2 in vivo and blocks MDM2-induced degradation of p53. The end result of these actions appears to be the enhancement of p53-related functions such as transactivation (reporter assays, FIG. 9D), growth inhibition (Kamijo et al., 1997a, Cell 91, 649–659) and possibly apoptosis (lens studies, FIG. 10) (see model in FIG. 11B). The inventors believe that their studies provide genetic evidence, in addition to physical data, that p19$^{ARF}$ acts primarily on the level of MDM2 rather than p53. The conceptual basis for this argument rests on the fact that although MDM2 overexpression acts to neutralize p53, p19$^{ARF}$ can still inhibit oncogenesis in this setting (FIG. 9A). In contrast, other oncoproteins that can neutralize p53 render cells refractory to p19$^{ARF}$ suppression (FIG. 6B). Thus, the inventors propose that either (i) p19$^{ARF}$ can interfere with the ability of MDM2 to neutralize p53 (FIG. 11B) or (ii) p19$^{ARF}$ can affect as yet undetermined MDM2-specific transformation functions beyond those regulating p53 levels and activity. The latter, although formally possible, appears less likely in light of mouse knockout studies suggesting that MDM2 functions primarily (if not exclusively) as a modulator of p53 function (Jones et al., 1995, Nature 378, 206–208). Regardless of the precise mechanism, the physical and functional link forged between p19$^{ARF}$ and the p53 pathway, along with the previously established one between p16$^{INK4a}$ and Rb (Quelle et al., 1995a, Oncogene 11, 635–645; Serrano et al., 1993, Nature 366, 704–707) provide for a "one-gene-two products-two pathways" hypothesis (FIG. 11A) that can explain (i) the exceedingly high rate of INK4a gene deletion in many human tumors and their derivative cell lines (Kamb et al., 1994, Science 264, 436–440) and in mouse melanomas (Chin et al., 1997, Genes and Development 11, 2822–2834) and (ii) the strong connection between tumorigenesis and the INK4a gene as opposed to other genes encoding cyclin-dependent kinase inhibitors (CKIs), such as INK4b, p21$^{CIP1}$ and p27$^{KIP1}$ (CordonCardo, 1995, Am. J. Pathol. 147, 545–560). Specifically, mice lacking INK4b exhibit a very low incidence of spontaneous tumor formation (E. Latres, C. Cordon-Cardo, and M. Barbacid, unpublished), p21$^{CIP1}$-deficient mice remain tumor-free (Elledge et al., 1996, TICB 6, 388–392), and although p27$^{KIP1}$-deficient mice can develop intermediate lobe pituitary hyperplasia or adenoma, these neoplasms rarely progress to malignant pituitary tumors (Elledge et al., 1996, TICB 6, 388–392). Similarly, in human cancers, the frequent alteration of INK4a contrasts sharply with an overall lower rate of INK4b mutation/deletion (Cordon-Cardo, 1995, Am. J. Pathol. 147, 545–560) and infrequent mutations in p21$^{CIP1}$ and p27$^{KIP1}$ (Cordon-Cardo, 1995, Am. J. Pathol. 147, 545–560). What makes the INK4a gene so unique among the CKIs with respect to tumorigenesis? In essence, two functionally distinct tumor suppressor pathways can be disabled by a single mutational event at the INK4a locus, this by virtue of its unique genetic organization. Stated differently, INK4a's potent tumor suppressor activity likely results from its ability to encode two unrelated anti-oncogenic proteins with cooperating modes of action (FIG. 11A).

Based upon the documented growth arresting activity encoded by the INK4a gene products (Serrano et al., 1993, Nature 366, 704–707; Quelle et al., 1995b, Cell 83, 993–1000) and the reduction in apoptosis in the lenses doubly null for Rb and INK4a (see FIG. 10 above), the inventors suggest that the mechanisms of tumor suppression by INK4a parallel those established for Rb and p53. Specifically, the collaborative consequences of loss of p16$^{INK4a}$ and p19$^{ARF}$ are deregulated cell proliferation as well as deactivation or attenuation of p53-dependent apoptosis which normally serves to promote the efficient elimination of these pre-malignant cycling cells. In agreement with this hypothesis is the observation that tumors arising in INK4a-deficient mice exhibit high proliferative indices and very low rates of apoptosis despite an intact p53 gene (CCC and RD, unpublished observations).

One prediction of this hypothesis is that tumors deficient for both p16$^{Ink4a}$ and p19$^{ARF}$ would be less likely to harbor Rb or p53 mutations. Furthermore, p19$^{ARF}$-sparing INK4a mutations could be associated with alterations involving other components of the p53 pathway (e.g., MDM2 gene amplification or loss of p53 function). It is important to emphasize that elimination of p19$^{ARF}$ may not preclude p53 mutation since p19$^{ARF}$ tumor suppressor activities are unlikely to overlap fully with those of p53. This lack of equivalence is made evident by the much higher level of genetic instability in p53–/– MEFs compared with INK4a–/– MEFs (Kamijo et al., 1997) (and NL and RD, unpublished) and by the higher rate of spontaneous tumor formation in p53–/– mice versus Ink4a–/– mice (Serrano et al., 1996, Cell 85, 27–37; Jacks, 1994). In the lens, the level of reduction in apoptosis achieved with loss of Ink4a function was less than that reported previously with loss of p53 (Morgenbesser et al., 1994) (reduction of 50 to 60% for Rb–/–, Ink4a–/– versus 75 to 85% for Rb–/–, p53–/–). Notwithstanding, loss of function mutations of p19$^{ARF}$ would be predicted to decrease the frequency of tumor-associated p53 mutations.

What is claimed:

1. A method for inhibiting growth of a tumor cell comprising directly injecting into a tumor a tumor cell growth inhibiting amount of p53 and an amount of a mammalian $p^{19ARF}$ effective to reduce degradation of p53 by endogenous MDM2, and thereby inhibit growth of the tumor cell, wherein the $p19^{ARF}$ is capable of blocking MDM2's ability to target p53 for degradation, wherein the mammalian $p19^{ARF}$ is a mouse $p19^{ARF}$ or a human $ps19^{ARF}$, and wherein the $p19^{ARF}$ and p53 are introduced to the cell by the introduction and expression of nucleic acids encoding $p19^{ARF}$ and p53 into the cell.

2. The method of claim 1 wherein the mammalian $p19^{ARF}$ is a human $p19^{ARF}$.

* * * * *

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: primer for MDM2 mutant

<400> SEQUENCE: 1
cgccatctag accggatctt gatgctggt                29

-continued

```
<210> SEQ ID NO 2
<211> LENGTH: 18
<212> TYPE: DNA
<213> ORGANISM: Artificial Sequence
<220> FEATURE:
<223> OTHER INFORMATION: primer for MDM2 mutant

<400> SEQUENCE: 2
cgaagggccc aacatctg                                                 18
```